(12) United States Patent
Jamiolkowski et al.

(10) Patent No.: US 10,828,018 B2
(45) Date of Patent: Nov. 10, 2020

(54) METHODS AND DEVICES FOR FORMING BIOMEDICAL COATINGS USING VARIABLE MIXING RATIONS OF MULTI-PART COMPOSITIONS

(71) Applicant: Ethicon, Inc., Somerville, NJ (US)

(72) Inventors: Dennis D. Jamiolkowski, Long Valley, NJ (US); An-Min Jason Sung, Warren, NJ (US); Leo B. Kriksunov, Ithaca, NY (US)

(73) Assignee: Ethicon, Inc., Somerville, NJ (US)

( * ) Notice: Subject to any disclaimer, the term of this patent is extended or adjusted under 35 U.S.C. 154(b) by 58 days.

(21) Appl. No.: 16/106,278

(22) Filed: Aug. 21, 2018

(65) Prior Publication Data

US 2018/0368824 A1     Dec. 27, 2018

Related U.S. Application Data

(62) Division of application No. 14/199,173, filed on Mar. 6, 2014, now Pat. No. 10,085,729.

(51) Int. Cl.
*A61B 17/00* (2006.01)
*A61M 11/00* (2006.01)
(Continued)

(52) U.S. Cl.
CPC ... *A61B 17/00491* (2013.01); *A61M 5/16827* (2013.01); *A61M 11/00* (2013.01);
(Continued)

(58) Field of Classification Search
CPC .... A61B 17/00491; A61B 2017/00495; A61B 2017/00522; A61L 24/00; A61L 24/0026;
(Continued)

(56) References Cited

U.S. PATENT DOCUMENTS 3,303,970 A   2/1967   Breslau
3,477,431 A   11/1969  Walecka
(Continued)

FOREIGN PATENT DOCUMENTS

CN        2554121 Y       6/2003
DE    2020/13000482 U1    7/2013
(Continued)

OTHER PUBLICATIONS

International Preliminary Report on Patentability dated Sep. 6, 2016 for PCT/US2015/017717.
(Continued)

*Primary Examiner* — Melanie R Tyson
(74) *Attorney, Agent, or Firm* — David R. Crichton; Leo Kriksunov

(57) ABSTRACT

The present invention relates devices capable of continuous and simultaneous expression of components of a multi-part biomedical composition with variable mixing ratios. The device has at least two syringes that contain the interreactive components of the multi-part biomedical composition. At least the barrel of the first syringe has a first retention compartment having a cross-sectional area dimension that is larger than the cross-sectional area of a second retention compartment. The first piston has a cross-sectional dimension that matches the inside cross-sectional dimension of the small dimensioned retention compartment, while a ring-shaped gasket is located within the large dimensioned retention compartment and has an outside cross-sectional dimension that matches an interior dimension of the large dimension retention compartment.

5 Claims, 23 Drawing Sheets

(51) Int. Cl.
*A61M 5/168* (2006.01)
*B05B 11/00* (2006.01)
*A61M 5/19* (2006.01)
*A61M 5/31* (2006.01)
*A61M 5/315* (2006.01)

(52) U.S. Cl.
CPC ...... *B05B 11/3059* (2013.01); *B05B 11/3083* (2013.01); *B05B 11/3084* (2013.01); *A61B 2017/00495* (2013.01); *A61B 2017/00522* (2013.01); *A61M 5/19* (2013.01); *A61M 5/3129* (2013.01); *A61M 2005/31598* (2013.01)

(58) Field of Classification Search
CPC .... A61M 5/16827; A61M 5/178; A61M 5/19; A61M 5/3129; A61M 2005/31598; A61M 11/00
See application file for complete search history.

(56) References Cited

U.S. PATENT DOCUMENTS

| | | | |
|---|---|---|---|
| 3,786,963 A | 1/1974 | Metzler | |
| 4,355,739 A | 10/1982 | Vierkoetter | |
| 4,432,469 A | 2/1984 | Eble | |
| 4,735,616 A | 4/1988 | Eibl | |
| 4,738,660 A | 4/1988 | Lucas | |
| 4,821,923 A | 4/1989 | Skorka | |
| 4,826,048 A | 5/1989 | Skorka | |
| 4,838,457 A | 6/1989 | Swahl | |
| 4,862,052 A | 8/1989 | Unsworth | |
| 4,993,594 A | 2/1991 | Becker | |
| 5,009,342 A | 4/1991 | Lawrence | |
| 5,041,088 A | 8/1991 | Ritson | |
| 5,152,431 A | 10/1992 | Gardner | |
| 5,152,461 A | 10/1992 | Proctor | |
| 5,224,627 A | 7/1993 | Weag | |
| 5,240,146 A | 8/1993 | Smedley | |
| 5,332,157 A | 7/1994 | Proctor | |
| 5,385,270 A | 1/1995 | Cataneo | |
| 5,402,916 A | 4/1995 | Nottingham | |
| 5,477,987 A | 12/1995 | Keller | |
| 5,599,312 A | 2/1997 | Higashikawa | |
| 5,634,571 A | 6/1997 | Cataneo | |
| 5,656,035 A | 8/1997 | Avoy | |
| 5,848,732 A | 12/1998 | Brugger | |
| 5,881,918 A | 3/1999 | Eichler | |
| 6,036,057 A | 3/2000 | Poutiatine | |
| 6,165,201 A | 12/2000 | Sawhney | |
| 6,179,862 B1 | 1/2001 | Sawhney | |
| 6,299,023 B1 | 10/2001 | Amone | |
| 6,464,107 B1 | 10/2002 | Brugger | |
| 6,514,534 B1 | 2/2003 | Sawhney | |
| 6,566,406 B1 | 5/2003 | Pathak | |
| 6,610,033 B1 | 8/2003 | Melanson | |
| 6,673,093 B1 | 1/2004 | Sawhney | |
| 6,818,018 B1 | 11/2004 | Sawhney | |
| 6,887,974 B2 | 5/2005 | Pathak | |
| 6,939,329 B1 | 9/2005 | Verkaart | |
| 6,968,982 B1 | 11/2005 | Bums | |
| 7,009,034 B2 | 3/2006 | Pathak | |
| 7,021,499 B2 | 4/2006 | Hansen | |
| 7,025,990 B2 | 4/2006 | Sawhney | |
| 7,057,019 B2 | 6/2006 | Pathak | |
| 7,192,604 B2 | 3/2007 | Brown | |
| 7,222,752 B2 | 5/2007 | Ponton | |
| 7,332,566 B2 | 2/2008 | Pathak | |
| 7,347,850 B2 | 3/2008 | Sawhney | |
| 7,351,224 B1 | 4/2008 | Shaw | |
| 7,592,418 B2 | 9/2009 | Pathak | |
| 7,686,191 B1 | 3/2010 | Bums | |
| 7,862,538 B2 | 1/2011 | Sawhney | |
| 7,872,068 B2 | 1/2011 | Khosravi | |
| 7,959,612 B2 | 6/2011 | Thompson | |
| 7,997,449 B2 | 8/2011 | Banco | |
| 8,003,705 B2 | 8/2011 | Sawhney | |
| 8,088,099 B2 | 1/2012 | McIntosh | |
| 8,454,559 B2 | 6/2013 | Fierkens | |
| 2002/0183616 A1* | 12/2002 | Toews | A61M 5/007 600/432 |
| 2003/0199816 A1 | 10/2003 | Ramming | |
| 2003/0233067 A1 | 12/2003 | McIntosh | |
| 2005/0261782 A1 | 11/2005 | Hoganson | |
| 2006/0253082 A1* | 11/2006 | McIntosh | A61B 17/00491 604/191 |
| 2009/0062741 A1 | 3/2009 | Smith | |
| 2010/0206808 A1 | 8/2010 | Maeda | |
| 2010/0206908 A1* | 8/2010 | Pruvot | B05B 11/3059 222/153.13 |
| 2012/0039959 A1 | 2/2012 | Tessmar | |
| 2012/0045651 A1 | 2/2012 | Myung | |
| 2012/0067984 A1* | 3/2012 | Matusch | A61M 5/1782 239/590 |
| 2013/0075428 A1 | 3/2013 | Brugger | |
| 2013/0172823 A1 | 7/2013 | Meron | |
| 2014/0031763 A1* | 1/2014 | Soma | A61M 5/19 604/208 |
| 2014/0144939 A1* | 5/2014 | Bertin | B05B 7/2486 222/135 |

FOREIGN PATENT DOCUMENTS

| | | |
|---|---|---|
| EP | 1433533 B1 | 9/2007 |
| EP | 1022060 B1 | 3/2010 |
| FR | 1054173 A | 2/1954 |
| GB | 1306126 A | 2/1973 |
| JP | H10234820 A | 9/1998 |
| JP | 54137703 A | 2/2000 |
| JP | 59028949 A | 7/2009 |
| WO | 1997/26086 A2 | 7/1997 |
| WO | 97/028834 | 9/2000 |
| WO | WO0009074 B1 | 9/2000 |
| WO | WO2006076247 A3 | 8/2006 |
| WO | WO2006076427 A3 | 9/2006 |
| WO | WO2008047032 A3 | 6/2008 |
| WO | WO2008053311 A3 | 2/2011 |
| WO | WO2010128394 A8 | 3/2011 |
| WO | WO2013017802 A1 | 2/2013 |
| WO | WO2013186736 A3 | 3/2014 |

OTHER PUBLICATIONS

International Search Report dated Jul. 21, 2015 for PCT/US2015/017717.

* cited by examiner

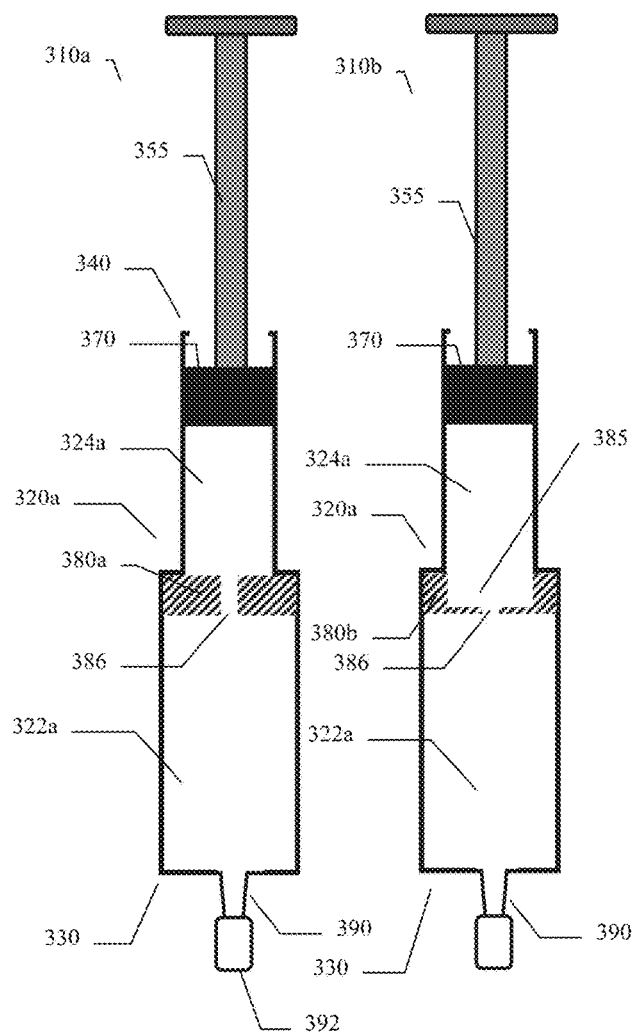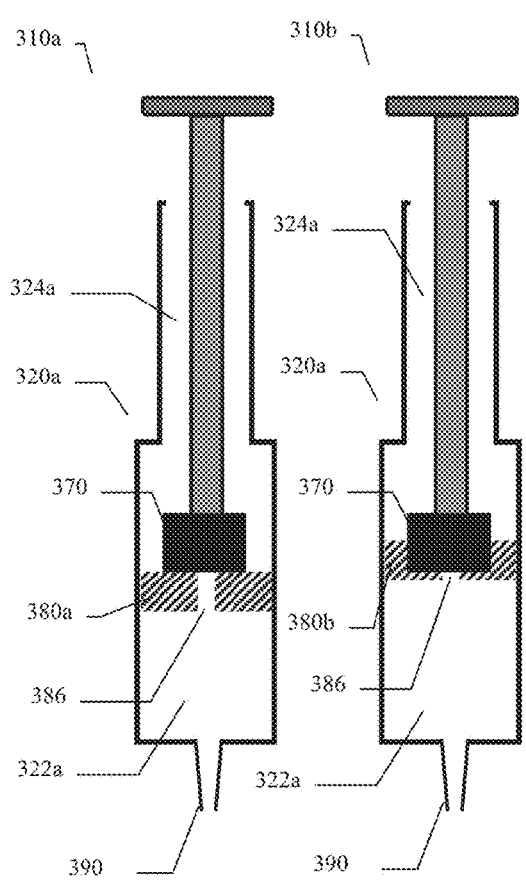
FIG. 8A  FIG. 8B  FIG. 8C  FIG. 8D

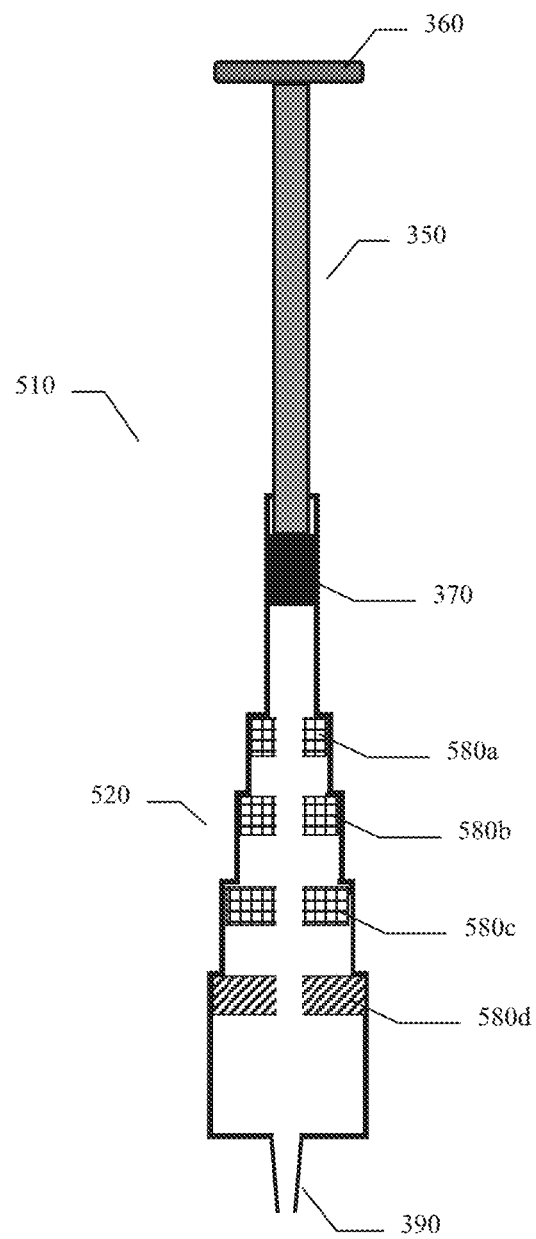

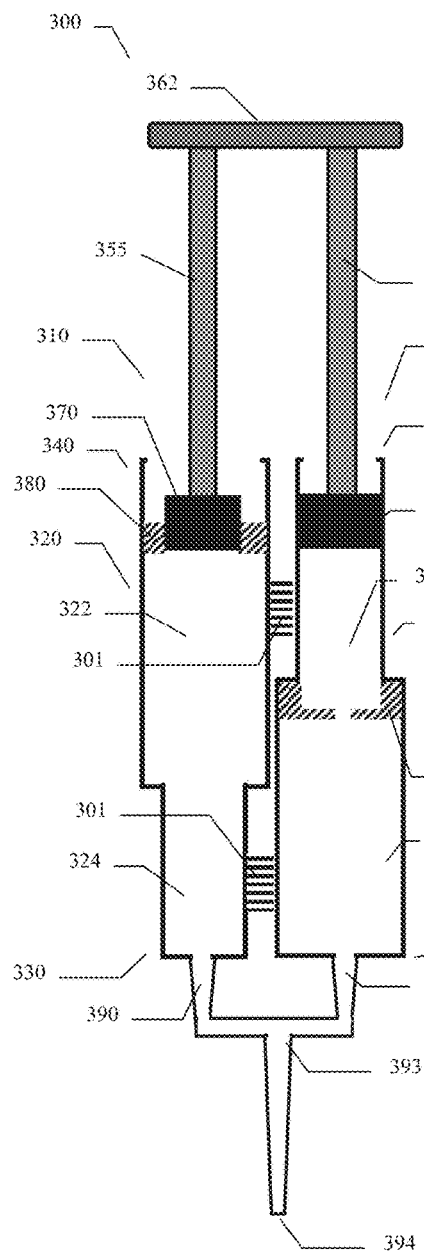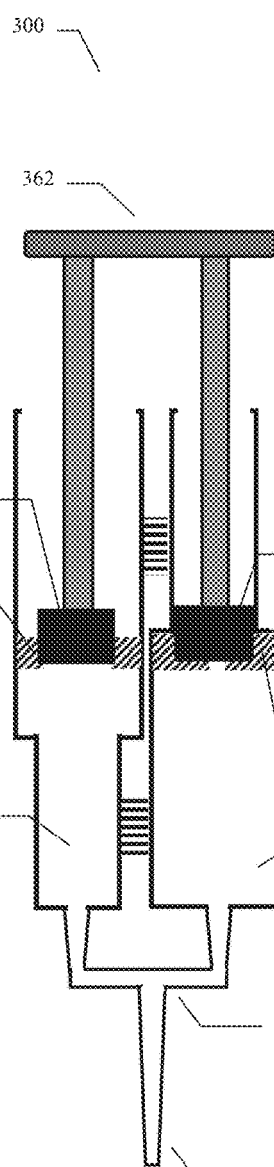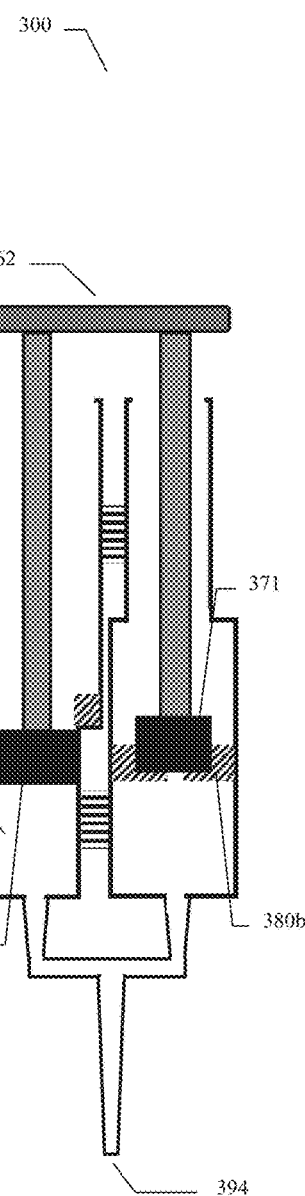

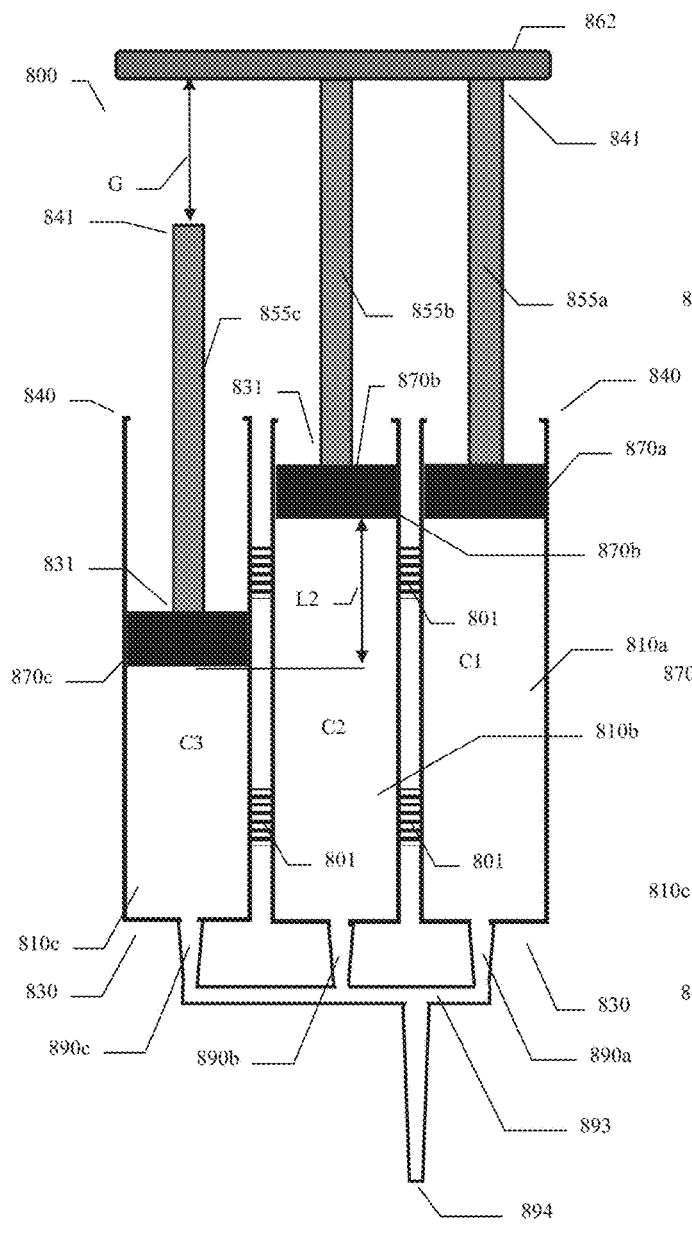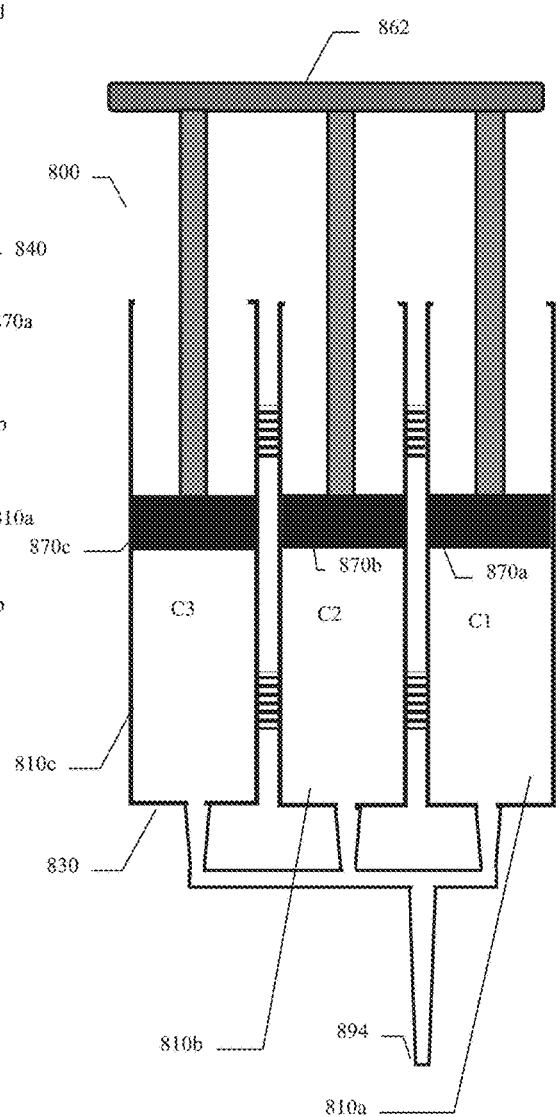

METHODS AND DEVICES FOR FORMING BIOMEDICAL COATINGS USING VARIABLE MIXING RATIONS OF MULTI-PART COMPOSITIONS

CROSS-REFERENCE TO RELATED APPLICATION

This application is a divisional application of co-pending U.S. application Ser. No. 14/199,173 filed on Mar. 6, 2014, the complete disclosure of which is hereby incorporated herein by reference for all purposes.

FIELD OF THE INVENTION

The present invention relates to biomedical coatings, including sealing agents, adhesives, hemostatic agents, and adhesions preventing coatings, more specifically to compositions and devices to deliver such coatings, whereby the composition of the coating and properties of the coating are variable across the thickness of the coating.

BACKGROUND OF THE INVENTION

Currently commercially available materials for biomedical coatings for the above mentioned applications, either synthetic or biological are typically capable of becoming non-flowable once applied onto bodily tissue. These include viscous gels with little or no further curing, as well as compositions that solidify or cure once applied. Cyanoacrylates products such as Ethicon's Dermabond® and Covidien's Indermil® are examples of tissue adhesives that possess high strength and cure in place. These materials polymerize to achieve the strength required, but do not offer the user any control of the degree of curing. Without the control of the degree of curing, they typically address only one clinical need, in this case to close and hold the incisions.

Other products such as Ethicon's synthetic Omnex™ and biological Evicel and Cryolife's BioGlue® are examples of sealants—that act as a sealant to prevent leakage. Again these materials typically address only one of the four clinical needs of acting as a sealant, acting as an adhesive, acting as a hemostatic agent, or acting as an adhesion preventing coating. Available products do not offer the user the option to change the performance characteristics to address a different clinical need. Products such as Ethicon's Intercoat, Genzyme's SepraGel®, Confluent's SprayGel®, and Covidien's SprayShield™, to name a few, are examples of adhesion barriers. These are either one of, or a combination of, hydrogels of PolyEthylene Glycol (PEG), Poly Vinyl Alcohol (PVA), CarboxyMethyl Cellulose (CMC), or HyaLuronic Acid (HLA). Once again these materials typically only address one of the four clinical needs already discussed, in this case to act as an adhesions preventative. As before, these materials do not offer user the option to change the performance characteristics to address a different clinical need.

Although there may be some materials with properties mid-way between sealants and adhesion preventatives, their properties are not optimized for either application and they cannot be changed by the surgeon at the time of application during surgery. Many of the solutions that the art provides in the four areas of surgical adhesives, sealants, adhesion preventatives and hemostatic agents are based on cross-linkable systems. Initially flowable to allow application to the surgical site to be treated, the product becomes non-flowable once applied; that is, it stays in place to function properly.

The performance characteristics of the hydrogel products are intimately related to cross-link density. When cross-link density is high, mechanical strength is high and (water) swellabilty is low. High cross-link density hydrogels are often associated with products that function as adhesives. Sealants often require slightly less mechanical strength; therefore hydrogels products in this class category can have cross-link densities that are concomitantly slightly lower. Finally a class of surgical adhesion preventatives based on hydrogel technology is cross-linked at a much lower level than the other two product classes. Their lower cross-link density allows a much greater amount of swellability leading to a very slippery behavior. This latter characteristic has been identified by some to contribute to the ability to prevent viscera from adhering to one another or the initiation of collagen deposition leading to adhesion formations. Likewise, clinically relevant properties of some hemostatic agents depend on the mixing ratios of components. For example, the mixing ratios of fibrinogen and thrombin alter the properties of the resulting matrix.

It is clear that all the products mentioned above offer pre-determined properties to address one clinical need only. There is no flexibility or choice for the physician to alter or dial in the properties for other clinical needs at the time of application during surgery.

There are many patent and open literature references that describe the formation of hydrogels based, wholly or in part, on PEG derivatives. Multi-armed PEGs are of particular interest. They have been made highly reactive when end-capped with electrophilic moieties; they react very quickly, for example, with nucleophilic species such as amines. The nature of these nucleophile-containing materials varies. In one case, they can be proteins, which normally contain an abundance of primary amines and other groups available for reaction. A second strategy is to have the nucleophile-containing material totally synthetic in nature. An example of the latter is a multi-armed PEG in which the arms are terminated in amine groups, especially primary amines. Trilysine is another example of a nucleophile-containing material, a compound that contains four amines, three of which are primary. These two classes of materials, the nucleophiles and the electrophiles, are often presented at the time of application as aqueous solutions of given concentrations. They are initially stored separately to prevent unwanted reaction prior to application.

Important hydrogel properties that can be altered by formulation include mechanical properties (e.g. tensile strength, modulus, elongation-to-break) and adhesive properties (e.g. adhesive and cohesive strength). Biological responses such as tissue reaction, protein deposition, as well as absorbability, can be altered or adjusted. Of particular interest are formulations that can render a hydrogel useful as a surgical adhesive, a surgical sealant, surgical adhesion barrier, or a hemostat. Because of the wide range of formulations available, there is generally a wide range of properties available. However with all these formulations available, one has not been identified that will simultaneously provide the properties necessary to act as an excellent surgical sealant as well as an excellent surgical adhesion preventative. Again, it is an object of this disclosure to specify designs that impart devices to deliver hydrogels with variable selectable-at-time-of-application compositions. Of particular advantage is providing a gradient in the coating orthogonal to the surface of the bodily tissue. In other words, providing a coating comprising a hydrogel which changes in composition, and thus in properties important for the surgical application, as a function of the distance away from the tissue upon which it is applied.

U.S. Pat. Nos. 6,514,534 and 7,025,990 "Methods for forming regional tissue adherent barriers and drug delivery systems" describe methods for forming hydrogel barriers in situ that adhere to tissue and prevent the formation of post-surgical adhesions or deliver drugs or other therapeutic agents to a body cavity. The hydrogels are crosslinked, resorb or degrade over a period of time, and may be formed by free radical polymerization initiated by a redox system or thermal initiation, or by an electrophilic-nucleophilic mechanism, wherein two components of an initiating system are simultaneously or sequentially poured into a body cavity to obtain widespread dispersal and coating of all or most visceral organs within that cavity prior to gelation and polymerization of the regional barrier. The hydrogel materials are selected to have a low stress at break in tension or torsion, and so as to have a close to equilibrium hydration level when formed.

U.S. Pat. No. 6,818,018 "In situ polymerizable hydrogels" discloses compositions and methods for forming hydrogels in situ through a combination of physical and chemical crosslinking processes in which physical crosslinking is mediated by one or more natural or synthetic components that stabilize the hydrogel-forming precursor solutions at a deposition site for a period of time sufficient for more resilient chemical crosslinks to form. Methods of using such hydrogels as tissue coatings to prevent postsurgical adhesion formation, as tissue augmentation or luminal occlusion aids, as matrices for carrying cells, drugs or other bioactive species, as tissue sealants or adhesives, and as medical device coatings also are provided.

U.S. Pat. No. 6,887,974 "Crosslinking agents and methods of use" describes polymeric crosslinking agents that have an inert water soluble polymeric component, biodegradable components, functional components reactive with chemical groups on a protein, for example, amine or thiol groups. The inert polymeric component may be flanked at each end with a biodegradable component which is flanked at each end with a protein reactive functional component. A polymeric crosslinking agent is disclosed having a biodegradable component, polyalkylene oxide, and at least three reactive functional groups that are each capable of forming a covalent bond in water with at least one functional group such as an amine, thiol, or carboxylic acid.

U.S. Pat. No. 7,057,019 "Crosslinked albumin hydrogels" describes materials, methods, and compositions for making crosslinked albumin hydrogels. Embodiments include a biocompatible material of albumin crosslinked with an n-functional crosslinking agent wherein n is at least 3. Other embodiments include a cross-linking agent having a polyalkylene oxide member. Other embodiments include a system for administering an albumin material, the system having albumin and a crosslinking agent that reacts with the albumin to form a crosslinked material made of crosslinked albumin. Another embodiment is a method of making a biocompatible material that includes a step of mixing albumin with an n-functional crosslinking agent wherein n is at least 3.

U.S. Pat. Nos. 6,566,406 and 7,009,034 "Biocompatible crosslinked polymers" disclose biocompatible crosslinked polymers that are formed from water soluble precursors having electrophilic and nucleophilic groups capable of reacting and crosslinking in situ. Methods for making the resulting biocompatible crosslinked polymers biodegradable or not are provided, as are methods for controlling the rate of degradation. The crosslinking reactions may be carried out in situ on organs or tissues or outside the body.

U.S. Pat. Nos. 7,332,566 and 7,592,418 "Biocompatible crosslinked polymers with visualization agents" disclose biocompatible crosslinked polymers that are formed from water soluble precursors having electrophilic and nucleophilic functional groups capable of reacting and crosslinking in situ. Methods for making the resulting biocompatible crosslinked polymers biodegradable or not are provided, as are methods for controlling the rate of degradation. The crosslinking reactions may be carried out in situ on organs or tissues or outside the body.

U.S. Pat. No. 8,003,705 "Biocompatible hydrogels made with small molecule precursors" discloses biocompatible crosslinked polymers formed from water soluble precursors having electrophilic and nucleophilic functional groups capable of reacting and crosslinking in situ.

U.S. Pat. No. 7,872,068 "Materials formable in situ within a medical device" discloses forming a material in situ by introducing into a space within a patient a water soluble polymer precursor of at least about 10,000 molecular weight solubilized in a flowable aqueous solution. Functional groups on the polymer precursor undergo covalent bonding in situ to form a solid and non-biodegradable material having a swellability of less than about 20% v/v and a Young's modulus of at least about 100 kPa within about 30 seconds to about 30 minutes of initiating a chemical reaction of the functional groups to form the solid material.

U.S. Pat. No. 6,610,033, "Dual component medicinal polymer delivery system and methods of use" discloses apparatus and methods for making and using a medicinal polymer formed from two components. The apparatus includes a double syringe holder housing first and second syringes that is adapted to be coupled with a predetermined orientation to a double vial holder housing first and second vials. The double syringe holder and double vial holder have mating key features that prevent the first syringe from coupling to the second vial and the second syringe from coupling to the first vial. The apparatus also includes a delivery device having first and second inlet ports and a key feature that prevents the first syringe from coupling to the second inlet port and the second syringe from coupling to the first inlet port.

U.S. Pat. No. 7,862,538 "Surgical delivery system for medical sealant" discloses systems for packaging dual or multiple-component adhesive systems that provide enhanced convenience and efficacy. In one aspect, the components of such a system may be divided into containers that allow for foolproof mixing schemes to avoid mixing the wrong components while also providing a sterile surface for mixing materials, with the sterile surface having optimal physical properties for mixing the materials, especially in small amounts. Certain embodiments include a surgical delivery system for a medical sealant including a packaging system with a detachable a sterile surface for mixing the sealant as needed for application.

U.S. Pat. No. 6,165,201 "Method and apparatus for in situ formation of hydrogels" discloses methods and apparatus of forming in situ tissue adherent barriers by using a sprayer capable of applying two or more viscous crosslinkable solutions to tissue. The sprayer comprises separate spray nozzles for each of two or more crosslinkable solutions, wherein each nozzle is either surrounded by an annular gas flow outlet or in communication with a gas-pressurized chamber, and also may include valves that prevent backflow through the supply lines carrying the crosslinkable solutions, and a venting system for venting excess pressure for laparoscopic applications In the presence of gas flow, the crosslinkable solutions are atomized and mixed to form a spray. Multi-component hydrogel systems suitable for use with the inventive methods and apparatus are also described.

U.S. Pat. No. 6,673,093 "Methods and apparatus for in situ formation of hydrogels" discloses methods and apparatus of forming in situ tissue adherent barriers using a sprayer capable of applying two or more viscous crosslinkable components to tissue. The sprayer comprises separate spray nozzles for each of two or more crosslinkable solutions, with each nozzle surrounded by an annular gas flow outlet. Crosslinkable solutions are stored in separate compartments and communicated under pressure to the spray nozzles. In the presence of gas flow through the annular gas flow outlets, the crosslinkable solutions are atomized and mixed in the gas flow to form a spray. Multi-component hydrogel systems suitable for use with the inventive methods and apparatus are also described.

U.S. Pat. No. 7,347,850 "Adhesion barriers applicable by minimally invasive surgery and methods of use thereof" discusses biocompatible crosslinked polymers and methods for their preparation and use with minimally invasive surgery applicators. The disclosure includes compositions and methods for in situ formation of hydrogels using minimally invasive surgical techniques.

U.S. Patent Application No. 20050261782, "Anti-adhesion device" describes a construct that allows opposing tissues to form adhesions with either side of the construct, as part of the natural healing process. The construct however is multi-layered, wherein the space between the layers provides the protection from unwanted adhesions forming between and bonding separate tissues. In one embodiment, this space between layers of the construct may be developed spontaneously, that is the multiple layers are released by design after a finite time and the opposing tissues are free to move independent of each other, free of adhesions. It further discloses an implantable device for the prevention of adhesions comprising a plurality of layers, wherein said plurality of layers comprises at least an anterior layer and a posterior layer, said anterior and posterior layers each having an outer and inner surface, each of said anterior and posterior layers having a porosity comprising a plurality of pores, said porosity varying across the thickness of each of said anterior and posterior layers.

U.S. Pat. No. 7,192,604 "Implantable biodegradable devices for musculoskeletal repair or regeneration" discloses an implantable, biodegradable device, comprising a fibrous matrix, said fibrous matrix comprising first fibers A and second fibers B, wherein fibers A biodegrade faster than fibers B, fibers A and B are present in relative amounts and are organized such that the fibrous matrix is provided with properties useful in repair and/or regeneration of mammalian tissue, wherein one of fibers A and B comprises a biodegradable polymer and one of fibers A and B comprises a biodegradable glass, and wherein the fibrous matrix comprises a gradient structure comprising a transition in the relative concentration of fibers A to fibers B.

Published U.S. Patent Application No. 2012/0045651 "Hydrophobic and Hydrophilic Interpenetrating Polymer Networks Derived from Hydrophobic Polymers and Methods of Preparing the Same" discloses a composition of matter comprising a hydrophobic or hydrophilic (or both) interpenetrating polymer network (IPN) containing a non-ionic/ionic polymer and a hydrophobic thermoset or thermoplastic polymer, articles made from such composition and methods of preparing such articles. The invention also includes a process for preparing a hydrophobic/hydrophilic IPN or semi-IPN from a hydrophobic thermoset or thermoplastic polymer including the steps of placing an non-ionizable/ionizable monomer solution in contact with a hydrophobic thermoset or thermoplastic polymer; diffusing the monomer solution into the hydrophobic thermoset or thermoplastic polymer; and polymerizing the monomers to form a penetrating polymer inside the hydrophobic thermoset or thermoplastic polymer, thereby forming the IPN or semi-IPN. In some embodiments, the non-ionic polymer forms a concentration gradient from a first portion of the composition to a second portion of the composition.

Published U.S. Patent Application No. 2012/0039959 "Anti-Adhesion Alginate Barrier of Variable Absorbance" discloses mono- and bi-layer alginate post-surgical anti-adhesion barriers with tailored absorption profiles and non-migrating characteristics. Muco-adhesive properties of alginates in their solid state are used to localize the device, and lubricious properties of alginates in their liquid state are used to mitigate adhesion formation during wound healing. In addition, the design of the implant can be selected such that the crosslinking agent is released from the device under specific conditions and the absorbance profile modified. A medicinal agent may optionally be incorporated. The application further discloses modification of crosslink density, whereby constructs transition from an adhesive state to a slippery anti-adhesive state as a function of time, or alternatively, the implant is spatially differentiated, and manufactured with two sides of differing crosslink density. Other approaches to varying the properties of an alginate sheet include varying the composition of alginate itself.

PCT Application WO 2000/009074 "VARIABLE OUTPUT APPLICATOR AND METHOD FOR MULTI-COMPONENT BIOLOGIC FLUID AGENTS" discloses applicators for dispensing a range of different tissue sealants, for example fibrin sealants with different setting times, conditioning agents or therapeutic agents, has a manual selector for user easily to select different outputs. Various differential drive mechanisms are disclosed for selectively dispensing, different concentrations of fluids optionally with internal mixing, from two or three or more fluid sources, such as fluid reservoirs carried by the applicator. Interchangeable reservoirs and the option of controlling concentration by discharging one reservoir to waste are also disclosed. The application further discloses a variable output handheld fluid agent applicator for dispensing a multi-component fluid agent to a site of use, the applicator comprising: a) multiple fluid component sources for the multiple fluid components; b) a dispensing tip to deliver the fluid components to the site of use; c) a manually actuated agent delivery system communicating with the multiple fluid component sources to deliver the multiple fluid components to the dispensing tip, and d) a manually operable selector coupled with the agent delivery system to select from available variation in the character of the fluid agent and enable a user to select a desired output; characterized in that the agent delivery system is variable to vary the character of the fluid agent dispensed and the delivery system provides an output of constant character after selection of a desired output.

U.S. Pat. No. 5,240,146 "Variable proportion dispenser" discloses a variable proportion dispenser which includes a housing which houses two pharmaceutical cartridges. A reciprocating drive assembly includes a drive stem extending from the piston of each cartridge, a sliding body mounted to the housing, and two one-way drive devices carried by the sliding body. Each one-way drive device includes a threaded dosage adjuster, and a reciprocating, one-way driver which drives the drive stem into the cartridge. The distance the reciprocating driver can move on the return stroke away from the cartridge is adjustable by changing the threaded position of the dosage adjuster within the sliding body to change if and when the opposed ends of the dosage adjuster and reciprocating driver disengage during the return stroke. During the next delivery stroke, the separated opposed ends do not contact for an initial portion of the stroke. The user can thus control the amount and proportion of each pharmaceutical dispensed during each delivery stroke for each dispensing cycle.

U.S. Pat. No. 5,152,461 "Hand Operated Sprayer With Multiple Fluid Containers" discloses a dispensing device or trigger sprayer which selectively draws fluid out from at least two containers, mixes the fluids in a desired concentration or ratio and expels the mixture of fluids out a nozzle. The trigger sprayer is equipped with a metering device for variably controlling the ratio of the fluids being mixed. The containers or bottles connected to the trigger sprayer are selectively detachable for refilling a container with fluid or exchanging one of the containers with another container having an alternate fluid.

British Patent No. GB 1306126 "HYPODERMIC SYRINGE BODY" claims a hypodermic syringe body for separately storing two components and permitting mixing in the syringe body and dispensing therefrom comprising: a barrel with a distal portion to receive a dispensing means, said barrel having at least two co-extensive channels in the wall thereof and parallel to the axis of the barrel, the ends of said channels being spaced from the ends of the barrel; a piston slideably mounted within said barrel and of axial length shorter than the axial lengths of the channels and positioned to separate said barrel into two non-communicating chambers said piston having a dose sliding fit in said barrel and when adjacent to said channels permitting ready flow of a liquid therethrough, the channels being of dimensions permitting ready flow of a liquid past the piston; a rupturable hermetic seal of a polymeric material applied to seal the piston to the barrel and resistant to rupture except by rotation of the piston; a plunger positively locked to said piston, extending proximal thereof; a plug at the proximal end of the barrel through which said plunger extends, said plug and said plunger being constructed to permit rotation of at least said plunger in said barrel; a hermetic seal between said plunger and said plug; and a hermetic seal between said plug and said barrel, at least one of said last two seals being a rupturable seal of a polymeric material applied to form said seal.

U.S. Pat. No. 4,735,616 "Arrangement for applying a tissue adhesive" discloses an arrangement for applying a tissue adhesive based on human or animal proteins, to seamlessly or seam-supportingly connect human or animal tissue or organ parts by uniting with blood-clot-promoting coagulation factors (thrombin). The arrangement includes a plurality of syringe bodies commonly actuatable by pistons and to which a connecting head is attachable. The syringe bodies have equal effective strokes, yet one of them, i.e., that destined to contain the protein solution, has a cross sectional area that is two to nine times larger than the other one(s). There may be applied tissue adhesives having a fibrinogen content of from 2 to 12%.

U.S. Pat. No. 8,088,099 "Fluid dispenser" discloses dispensing assemblies, methods, and kits of parts for dispensing two separate fluids to an treatment site, including entraining non-atomized flow of a first fluid in an atomized flow of a second fluid, delivering a first fluid upstream from a second fluid, delivering a first fluid and a second fluid with re-shapeable malleable tubes, delivering first and second fluids with releasable connectors maintained by a handle assembly, and kits of parts with angularly offset pockets.

U.S. Pat. No. 7,959,612 "Dual syringe injector system" discloses devices and methods for simultaneous injection or delivery of two or more substances from separate syringes. The syringes are loaded into a device that has a handle and a screw driven mechanism for simultaneously depressing the plungers of the syringes. The user grasps the handle and positions the device. Thereafter, the screw mechanism is used to simultaneously advance the plungers of the syringes thereby simultaneously expelling the substances from the syringes.

U.S. Pat. No. 6,939,329 "Apparatus for holding and operating one or more syringes" discloses an apparatus for supporting a syringe which includes a handle portion and a cradle. A clip is provided for connecting the plungers of two or more syringes, and two or more syringes are operated by placing one in the cradle and attaching the clip to the plungers for simultaneous operation of the plungers. The handle portion also forms a cavity for storing the clips. The apparatus is preferably used in combination with an applicator tip that combines the outputs from the two or more syringes.

Published U.S. Patent Application No. 2009/0062741 "Dual lumen syringe" discloses a dual lumen syringe which includes a body having a pair of elongate cavities or lumens formed therein. A directional valve is associated with each lumen. The valve is alternated between the first position wherein the lumen is communicably connected to a fluid inlet and a second position wherein the lumen is connected with a fluid outlet. There are a pair of elongate plungers, which are fixedly interconnected by a handle. Each plunger is received and longitudinally slidable in a reciprocating manner through a respective lumen. The valves are switched to a first position wherein the lumens are interconnected with the fluid inlets and the plunger is retracted to aspirate fluids through the respective inlets and into the lumens. The valves are then switched to a second position to communicably interconnect the lumens with the outlets. The plungers are then simultaneously driven inwardly through the respective lumens to drive the fluids simultaneously through the outlets to a dispensing tip permanently connected to the body and in communication with the outlets.

U.S. Pat. No. 5,599,312 "Syringe" claims a syringe comprising: a cylinder, having a connection portion for a syringe needle at a first end and an opening at a second end; and a plunger to be inserted into the cylinder from the opening, wherein a plurality of partitions are slidably provided between said connection portion and said plunger within said cylinder to divide an internal space of said cylinder into plural watertight chambers, wherein between adjacent partitions or between one of said partition and said plunger, two or more chambers are formed, wherein the chambers are filled with respective injection agents, and a passage formed integrally with the cylinder and communicating each of said chambers with said connection portion is provided without distorting said partitions when said plunger is moved within said cylinder toward said first end.

U.S. Pat. No. 3,477,431 "COMBINED MIXING SYRINGE AND CONTAINER", claims a combined syringe and plural compartment container comprising: an elongated syringe barrel having a delivery end and an open end and an enlarged portion of greater diameter than the syringe barrel extending around its periphery at a point intermediate its ends; a plunger slidably disposed within said syringe barrel, said plunger having at least one piston affixed thereto, the piston slidably and sealingly engaging the syringe barrel and defining, with the syringe barrel, at least one compartment on either side of said enlarged portion of the syringe barrel; sealing means closing the delivery end of the syringe barrel; a cover closing the open end of the syringe barrel, said cover having an opening therein, the plunger extending through said opening in the cover and having a slot in the shaft thereof immediately adjacent to the cover when the plunger is in the extended position.

U.S. Pat. No. 8,454,559 "Hypodermic syringe with retractable needle" discloses hypodermic syringe having a barrel which with an inner wall thereof defines a reservoir, a closing-off device near the first end of the barrel, and a plunger that is movably placed in the second end of the barrel, wherein the closing-off device comprises a circumferential wall that sealingly abuts the inner wall of the barrel, at the side facing away from the nozzle is provided with a recess extending along a centre line of the closing-off device and over the full width thereof, which recess merges into the through-opening, with in the recess two diametrically opposite flexible locking members, extending in the longitudinal direction of the recess and towards the inner wall, which locking members engage into diametrically placed locking grooves in the inner wall, and at the side facing away from the nozzle, at a circumferential part of the closing-off device situated outside of the recess, is provided with two diametrically opposite and radially outwardly extending blocking members, that engage in diametrically placed blocking grooves in the inner wall.

U.S. Pat. No. 7,351,224 "Retractable syringe assembly designed for one use" discloses a syringe assembly having a retractable needle, the syringe assembly being rendered unusable after a single injection and having a hollow syringe body, a retraction mechanism with a spring disposed in the front portion of the syringe and an inner head, a continuous retainer member surrounding the inner head, and a bridging portion disposed between the continuous retainer member and the inner head, wherein the bridging portion couples the continuous retainer member and the inner head to form a fluid seal between a fluid passageway and the barrel prior to retraction, and a plunger reciprocally disposed inside the barrel and forming a variable chamber between the plunger and the needle holder prior to and during retraction, wherein the continuous retainer member is releasable from the inner head of the needle holder when the plunger is further depressed inside the barrel following injection.

Japanese Patent Application JP59028949 "APPARATUS FOR SAMPLING BLOOD" discloses a device for blood sampling or for use as a hypodermic syringe consists of a holding arrangement for receiving syringe barrels of varying size and has a metering facility which makes it possible for different metering volumes to be set for drawing-up of a reagent. The holding arrangement for receiving syringe barrels of varying size is, in a first embodiment, provided with several rings running concentric to one another and to which syringe barrels of varying diameter can be attached, and, in a second embodiment, with several parallel slots into which syringe barrels of varying diameter and size can be inserted by means of flange sections. The facility for metering adjustment has a unit with guide curves and cams which can be adjusted relative to one another and, as a function of their setting, limit the movement of the plunger in the direction of the opening of the syringe barrel for receiving the point of the needle.

U.S. Pat. No. 5,477,987 "DISPENSING APPLIANCE FOR AT LEAST TWO COMPONENTS" discloses a dispensing appliance for at least two components which comprises a respective pump assembly for each component, each of said pumps being connected to a detachable container holding one of said components, and the pump outlets ending in a common but divorced outlet. Said pump assemblies are held in a frame which can be dismantled and reassembled, and the cylinders of said pump assemblies are composed of different segments.

U.S. Pat. No. 5,656,035 "REFILLABLE FIBRINOGEN DISPENSING KIT" discloses a refillable dispenser for separately dispensing each of two biological fluids contained therein for intermixing at a site outside of the dispenser to produce hemostasis or a tissue adhesive. The dispenser is compact, contains integrally formed internal reservoirs for the two biological fluids, an injection port on each reservoir for refilling the reservoir, and is designed for efficient filling without compromising the integrity of the sterile field. The dispenser is capable of dispensing the biological fluids, such as fibrinogen and thrombin, at either a focused point or in an aerosol mist In addition, spray elements are disclosed for uniformly distributing the two biological fluids along either the interior surface or the exterior surface of an implantable vascular graft.

U.S. Pat. No. 4,355,739 "Liquid storage container" discloses a liquid storage container that can be connected or attached to a spray pump which comprises two separate chambers to hold liquid components, each chamber having a take-up tube which leads to a mixing chamber contained within a movable member attached to a movable external selector, the member having openings therein, wherein, when the external selector is moved, the movable member attached thereto moves in a manner such that the ratio of the quantities of liquid components from the chambers varies.

U.S. Pat. No. 5,402,916 "Dual chamber sprayer with metering assembly" discloses a hand-actuated multiple-container trigger sprayer includes a sprayer head assembly removably connected to a plurality of fluid containers. The sprayer head assembly has an outer housing, a nozzle attached to the housing, pump mechanism enclosed within the housing, and tubing fluidly connecting each of the plurality of fluid containers with the pump mechanism in the housing. A trigger or lever actuates the pump mechanism to draw fluid through the tubing from each of the plurality of fluid containers and to discharge the fluid through the nozzle. A metering device is located between the fluid containers and the pump mechanism and is accessible externally from the housing to selectively control the amount of fluid drawn from the containers. The metering device includes flow paths to the pump mechanism for each of the fluid containers. The diameter and length of at least one of the flow paths can be controlled to selectively control the amount of fluid drawn from the fluid containers. The metering device within the spray head assembly allows user-selected ratios of fluid to be drawn from the containers and sprayed through the nozzle in the spray head. The patent further references examples of multiple-container trigger sprayers, U.S. Pat. Nos. 3,786,963; 4,355,739; 5,152,431.

U.S. Pat. No. 7,997,449 "Fluid delivery system for dispensing primary and secondary fluids" discloses a trigger operated fluid delivery system for dispensing two different fluids is disclosed. The fluid delivery system includes a first container having a first primary fluid, a fluid inlet conduit in fluid communication with the first container, and a pump for drawing the first fluid through the fluid inlet conduit and into a pump chamber. A fluid discharge conduit is located downstream of the pump chamber. The fluid discharge conduit is in fluid communication with the pump chamber and a discharge orifice. The pump discharges the first fluid from the pump chamber into the fluid discharge conduit. The fluid delivery system also includes a second container having a second fluid that delivers the second fluid into the fluid discharge conduit. The second fluid mixes with the first fluid when the first fluid is discharged into the fluid discharge conduit such that a mixture of the first fluid and the second fluid is discharged through the discharge orifice.

U.S. Pat. No. 3,303,970 "Device for simultaneously dispensing from plural sources" discloses improved mechanism for simultaneously dispensing several liquids; improved mechanism for varying the proportions of the several liquid constituents in the mixture before or during the dispensing operation; mechanisms having novel valve means for metering predetermined proportions of several liquids which are being simultaneously dispensed; and improved dispenser which permits varying the proportions of a dispensed liquid mixture to achieve optimum results.

U.S. Pat. No. 4,826,048 "Dispenser for manually discharging plural media" discloses a dispenser that has two facing and outwardly sealed reservoirs for separate media components, as well as for each reservoir a separate discharge pump, both discharge pumps being simultaneously operable by means of a common handle. The components are separately sucked in and are kept separate up to a mixing zone located inside or outside the handle, but with respect to the use thereof are brought together at the latest possible time. The components can be brought together in a precisely dosed quantity ratio.

U.S. Pat. No. 4,993,594 "A multi-constituent mixing and metering dispenser" discloses a multi-constituent mixing and metering dispenser adapted to yield a composition whose intermixed constituents are in relative proportions settable by the user. The extrudable constituents are stored in separate compressible pouches encased in face-to-face relation in the squeeze container of a supply section. Secured to the top of the container is a metering and mixing output section having a mixing chamber therein provided with an outlet. Each pouch has a flexible dip tube inserted therein leading to the mixing chamber in the output section. The container includes a check valve that is caused to close when the container is squeezed, thereby hermetically sealing the container and exerting pneumatic pressure on the pouches to cause extrusion of the constituents into the mixing chamber from which the resultant mixture is discharged through the outlet. Mounted in advance of the mixing chamber is a metering mechanism having a dial-turned shaft on which a series of cams is supported, each acting to pinch a respective tube to restrict flow of the related constituent into the mixing chambers. The cam arrangement is such that in the course of a full turn of the dial by the user, the relative proportions of the constituents are varied through a broad ratio range to produce a composition whose effective strength or other characteristic can be set by the user from a predetermined minimum value to a maximum value.

U.S. Pat. No. 5,152,461 "Hand operated sprayer with multiple fluid containers" discloses a dispensing device or trigger sprayer which selectively draws fluid out from at least two containers, mixes the fluids in a desired concentration or ratio and expels the mixture of fluids out a nozzle. The trigger sprayer is equipped with a metering device for variably controlling the ratio of the fluids being mixed. The containers or bottles connected to the trigger sprayer are selectively detachable for refilling a container with fluid or exchanging one of the containers with another container having an alternate fluid.

European Patent publication EP1022060 A2 "Method and apparatus for dispensing multiple-component flowable substances" discloses a sprayer apparatus for selectively spraying or dispensing multiple fluid components. The apparatus comprises a housing having a first inlet and a first outlet, the first housing inlet being adapted for attachment to a garden hose, the first housing outlet being in fluid communication with the first housing inlet; and an insert member having a first inlet for receiving fluid and a first outlet for dispensing fluid therefrom, the first insert inlet being in fluid communication with the first insert outlet through a passage defined by the insert member, the insert member being mateable with the housing so that the first housing outlet mates with the first insert inlet so that a fluid can flow from the first housing inlet to the first insert outlet. A method of spraying a fluid is also disclosed.

U.S. Patent publication No. 2013/0075428 "Dispenser" discloses a dispenser that provides measured doses of at least two components using a common pump. Each of the components is stored in its own separate container; each of which is connected to the common piston pump through an inlet valve. A metering device is disposed between the inlet valves and the pump chambers. The metering device is rotatable around an axis and controls the volume of each component disposed by either changing to flow rate of the component through its inlet valve or by changing the stroke length of the piston associated with its inlet valve. Preferably, the metering element is connected in a non-rotation manner (e.g. in form of a four cornered shaft) to the piston and the dispenser head, such that the adjustment of the desired dosage ratio is easily done by turning of the dispenser head. For a simple structure, the metering element includes holes or recesses of different size or a bent slot for changing the flow section and/or the flow length in an easy way. It is also possible to change the cross section of the respective inlet valve by a simple limitation of the respective valve opening.

U.S. Pat. No. 5,385,270 "Selectable ratio dispensing apparatus" discloses an apparatus for dispensing two flowable substances in a user selectable ratio having a container and a selector member. The container includes a dispensing end, a flexible continuous outer wall, and a flexible inner diaphragm separating the container into two generally equal chambers for each receiving a different flowable substance. Each of the chambers includes an end generally open proximate the dispensing end of the container. The selector member is disposed between the open ends of the chambers and the dispensing end of the container and includes a single opening extending therethrough. The selector member is selectively rotatable with respect to the container between a series of predetermined positions where the selector member opening is either in full registry, partial registry or not in registry with the open ends of each of the chambers such that upon compression of the outer container wall, a predetermined measure of flowable substance is dispensed from the dispensing end of the container with the ratio of the flowable substance from the two chambers which constitutes the predetermined measure being selectively variable.

U.S. Pat. No. 6,036,057 and PCT publication WO1997/026086 "Dual piston variable proportioning system" discloses a proportioning system which includes first and second cylinder and piston arrangements with an actuator operably engaging the first and second cylinder and piston arrangement. By changing the diameter and/or stroke of the pistons the mix ratio of two dispensed fluids changes. By changing the pivot point of the actuator, the stroke length can be changed. The proportioning system also includes a safety mechanism which prevents a concentrated fluid from being dispensed should the reservoir of diluting fluid be depleted. The embodiments provide for adjusting the proportioner to affect the mix ratio of the several fluids which are being mixed together and configurations for changing the proportioning ratios.

U.S. Pat. No. 5,009,342 "Dual liquid spraying assembly" discloses a dual liquid spraying assembly comprises an outer container containing at least two separate compartments for two different liquids, a spray pump dispenser for mounting on the outlet of the container, and a valve assembly mounted between the compartments and the spray pump dispenser for controlling the proportions of the different liquids dispensed. The valve assembly comprises an inner valve member having a discharge outlet for connection to the spray pump dispenser and at least two inlets for connection to the respective compartments, and an outer, control sleeve rotatably mounted on the inner valve member for controlling connection of the inlets to the outlet. Both the inner and outer valve members are releasably secured on the outlet of the container to extend co-axially with the outlet opening. Movement of the control member relative to the first valve member between the first and second positions gradually varies the relative sizes of the two inlets so as to vary the ratio of the two liquids dispensed.

U.S. Pat. No. 4,838,457 "Lotion blending and dispensing unit" discloses a lotion blending and dispensing unit for internally combining and then discharging a composite lotion or solution which includes a cylindrical housing having a storage chamber for enclosing at least a pair of lotion containers removably mounted on a mounting block. The block is provided with at least a pair of orifices on an annular surface having a central projection about which a selector dial rotates. The projection includes at least a pair of passageways in fixed alignment with the orifices so as to conduct lotion therethrough. A regulating disc is movably disposed on the annular surface for revolving about the projection whereby a plurality of different sized apertures may be selectively aligned between the orifices and the passageways. The disc is movable in response to rotation of the selection dial.

U.S. Pat. No. 4,432,469 "Device for discharging a plural-component material" discloses a device for discharging measured amounts of a plural-component material, such as an adhesive, filling, sealing or putty-like substance includes an axially extending casing having a first end. The interior of the casing is divided into separate compartments each having a discharge opening at the first end. A mixing chamber is positioned at the first end of the casing for receiving the components discharged from the compartments. A slide plate is positioned between the first end of the casing and the mixing chamber and is rotatable about the axis of the casing. The slide plate has openings for passageways alignable with the discharge openings for admitting selective amounts of the components into the mixing chamber. Due to this arrangement, the mixing ratio of the two components, contained in the compartments $1a$, $1b$ can be changed in the adjustment position bordering the locking position. The mixing ratio of the components also influences the hardening time of the resulting mixed substance.

U.S. Pat. No. 5,634,571 "Apparatus for dispensing two sprayable substances in a user selectable ratio" discloses an apparatus for dispensing two sprayable substances in a user selectable ratio. The dispensing apparatus comprises first and second pressurized containers for holding first and second sprayable substances. The dispensing apparatus further includes a manifold member having first and second inlet openings and an outlet opening. The inlet openings receive the dispensing ends of the first and second pressurized containers. The manifold member includes two passages which are in fluid communication between the first and second inlet openings and the outlet opening, respectively. A selector member having a single opening extending therethrough is provided in fluid communication with the first and second passages in the manifold member. The selector member is selectably rotatable with respect to the outlet opening in the manifold member. An actuator is provided for dispensing the sprayable substance from the apparatus with the ratio of the dispensed substance being selectably variable by the user from 100% of the first sprayable substance and 0% of the second sprayable substance in the first position to 0% of the first sprayable substance and 100% of the second sprayable substance when the selector member is in the second position, to any desired ratio therebetween when the selector member is in an intermediate position.

U.S. Pat. No. 6,464,107 "Dosage dispenser" discloses a proportioning dispenser for proportioning at least two components which are each supplied via a pump unit from an associated accommodating compartment is disclosed. The adjustment of the mixing ratio is effected via a transmission member the point of application of which is adjustable with respect to the two pump units. The actuation of the pump units is performed by a pivotable or displaceable transmission member the pivoting axle of which can be displaced relative to the operating members of the pump unit—for example the displacers. The position of the pivoting axle relative to the pump units is in this case selected to effect a change in the opposite direction, such that only the proportioning ratio of different components relative to one another is adjusted while the complete capacity preferably remains essentially constant. It is also conceivable, however, to adjust the complete displacement volume by adjusting the pivoting axle. Both components can be dispensed in a mixed or unmixed condition.

U.S. Pat. No. 5,224,627 "Metering pump dispenser for liquid and/or pasty media" discloses a metering pump dispenser that serves for simultaneous metered output of liquid and/or pasty media from at least two separate supply chambers, which are arranged in a common pump housing and to which are assigned individual separate metering pumps, each with an intake and output valve. The metering pumps are manually driven by a common actuating device, which extends on the side of actuation in a common front side of the metering pumps that are present and is provided with one or more output channels. Metering pumps each have as pump devices communication bellows which are joined on the housing side with pump housing and on the output side with the common actuating device. Actuating device is a lever-type device mounted in a swiveling manner around a swivel seat on one side in a head part of pump housing axially projecting over supply containers, for conducting limited pump strokes. Swivel axis of swivel seat is arranged crosswise to a common plane of symmetry of metering pumps, so that metering pumps have variable distances and variably large actuation levers to the swivel axis, and upon actuation of actuating device, pump strokes of different magnitude can be introduced in a specific, preselectable ratio at the same time and in the same direction.

U.S. Pat. No. 5,848,732 "Dispenser for a liquid medium consisting of two components" discloses a dispenser for a liquid medium consisting of two components. The dispenser in particular comprises two accommodation compartments for two different components of the material to be dispensed. Each of the accommodation compartments has an outlet and a mixer connected thereto. The mixer is manually adjustable by an adjuster and changes the ratio of the supplied components of the medium. Finally, the dispenser comprises a dispenser nozzle for the medium to be dispensed, which is connected to the mixer.

Japanese patent publication JP 54,137,703 "LIQUID RATIO VARIABLE CONSTANT CAPACITY DISCHARGE SYSTEM" discloses a system that targets making constantly optional miscible ratio adjustable by only necessary amount in the mixing material at high efficiency in such a way that fluidic material may be measured at optional ratio by easier operation giving facility for discharging it at constant amount. Crude material reservoirs are respectively connected through supply pipes to discharge devices which constitute a plunger pump. The discharge devices are equipped respectively with needle valves at intake ports and discharge ports and its hollow part has plungers respectively connected to one lever.

European patent publication EP 1,433,533 A1 "Dispensing apparatus having means for dispensing two products in variable ratios" discloses a dispenser for two fluid products in variable proportions that has two containers with separate pumps, push-button with outlet valve and regulator. The dispenser consists of two containers with separate pumps operated by a push-button with an outlet valve. The push-button is connected to the pumps by at least one flexible transmission member and a control element that can be adjusted by a regulator to set its end position and vary the proportions in which the products are dispensed from the containers according to the user's requirements.

U.S. Pat. No. 7,222,752 "Dispenser device including means that enable two substances to be dispensed in varying proportions" discloses a dispenser device that includes reservoirs for containing respective substances, pumps associated with respective reservoirs, and a pushbutton. The device allows two substances to be dispensed in varying proportions by actuating the pushbutton. In embodiments, each pump has a moving control member which, when actuated, causes the substance contained in the reservoir associated with the pump to be dispensed. In embodiments, at least one elastically-deformable transmission member is associated with a control member and is disposed in such a manner as to transmit displacement of the pushbutton to the control member in order to dispense substance. In embodiments, at least one adjustment member adjusts the end-of-stroke position of the displacement at least of the control member associated with the transmission member.

U.S. Pat. Nos. 7,686,191 and 6,968,982 "Multiple-mist dispenser" disclose dispenser that includes at least one container and at least one nozzle for dispersing the contents of the container(s). In one preferred embodiment, first and second nozzles functionally associated with sterilization agent within the container are positioned to disperse the sterilization agent to first and second target points respectively, the first target point being distinct from the second target point. In another preferred embodiment of the present invention, a grid is positioned in front of the nozzle(s) so that a dispersement of sterilization agent from within the container(s) sterilizes the grid(s) when the nozzle(s) are activated. Yet another preferred embodiment of the present invention is directed to a multiple-mist dispenser that includes a dual chamber activation sleeve so that two nozzles are simultaneously actuatable by depression of the dual chamber activation sleeve.

PCT publication WO2008/053311 "A SPRAYING DEVICE WITH LIQUID ADJUSTMENT MECHANISM" discloses a sprayer which comprises a spraying mechanism, at least two liquid containers, a liquid adjusting mechanism, and liquid feeding members; the spraying mechanism having a knob for activating a pump or releasing a valve for dispensing a liquid coming from an inlet to an outlet; the liquid feeding member has at least two liquid feeding tubes, one end of each of the at least two liquid feeding tubes is in liquid communication with each of the at least two liquid containers respectively, and the other end of each of the at least two liquid feeding tubes is jointed and connected to the inlet of the spraying mechanism; the liquid adjustment mechanism comprising two sets of adjoining sloped surfaces and sets of rollers are in contact with the two flexible portions of each of at least two liquid feeding tubes and when moving from right to left change sectional areas of the inside space of the flexible portions in such a way that amount of liquid supplied from each of the at least two liquid containers through each of the at least two liquid feeding tubes is adjusted. When flow of liquid from one feeding tube increases by the adjusting mechanism, the flow from the other feeding tube decreases in a way that the total amount of the liquid supplied by at least the two feeding tubes are substantially constant. In practice it is possible to mix two liquids such as two different perfumes with different fragrances or mix two different color paints to create a new fragrance and or paint color.

U.S. Pat. No. 6,299,023 "Device for dispensing two substances in a user selectable ratio with replaceable cartridges" discloses a device for dispensing a base substance and a booster substance in a user selectable ratio includes a dispenser head having a pair of spaced apart outlet ports, a first cartridge containing the base substance which is removably coupled onto the dispenser head and a second cartridge containing the booster substance which is removably coupled onto the dispenser head. Each of the first and second cartridges includes a collapsible plastic liner which is mounted onto a supporting frame, the supporting frame of each cartridge having a uniquely shaped flange. A first pump assembly is disposed within the dispenser head and serves to draw a fixed amount of the base substance from the first cartridge and dispense the fixed amount of base substance out one of the outlet ports upon depression of a trigger which is slidably disposed in the dispenser head. A second pump assembly is disposed within the dispenser head and serves to draw a fixed amount of the booster substance from the first cartridge upon depression of the trigger, dispense a user selectable percentage of the fixed amount of booster substance out the other outlet port and return the remaining percentage of the fixed amount of the booster substance back into the second cartridge.

U.S. Pat. No. 7,021,499 "Aerosol package" discloses an aerosol spray cleaner comprises two containers and a dispenser with a single dispensing spray outlet. One container has a cleaning composition and the other has an oxidizing composition. An integrally molded actuator includes a resiliently cantilevered lever connected to container valves to simultaneously open the valves to dispense the two fluids through the dispensing spray outlet. A handle extends laterally of the containers so grasp the handle and depress the actuator with a thumb. It further references manual trigger dispensers which are disclosed in U.S. Pat. Nos. 5,332,157, 4,862,052, 4,821,923 and 4,432,469.

SUMMARY OF THE INVENTION

The present invention, in one embodiment, relates to a device for uninterruptible simultaneous expression of components of a multi-part biomedical composition in varying mixing ratios, comprising a) a connecting means for support of at least two syringe barrels and device handling; and b) at least two syringes each containing a different component of the multi-part biomedical composition, each of said syringes positioned side by side and interconnected by the connecting means, each of said syringes further comprising plungers connected to each other at a distal end and having pistons attached to said plungers at a proximal end. The first syringe comprises a first retention compartment and a second retention compartment that are spaced axially from each other along a linear axis, wherein the first retention compartment has at least in part a larger cross-sectional dimension relative to the second retention compartment. The first piston located within the barrel of the first syringe has a first piston cross-sectional dimension that corresponds to an inside cross-sectional dimension of the second retention compartment. A ring-shaped gasket is located within the first retention compartment and has an outside dimension that corresponds to an interior dimension of the first retention compartment.

The present invention, in another embodiment, relates to a method for applying on tissue a coating having at least two physiologically distinct layers from a single device by delivery of a multi-part biomedical composition in different blended or mixing ratios comprising the steps of a) connecting at least two syringe barrels that contain inter-reacting components of the multi-part biomedical composition, with barrels each having a piston that is internally slidable for expression of said components, wherein at least a first syringe comprises a first retention compartment and a second retention compartment that are spaced axially therein with a gasket positioned in the first retention compartment; b) advancing the pistons through each syringe to express onto a surface the reactive components of the multi-part biomedical composition in a first blended or mixing ratio; c) continuing to advance the pistons to engage the gasket with the piston of a first syringe or to disengage the gasket from the piston of a first syringe at a point between the first retention compartment and the second retention compartment; and d) still further advancing the pistons through each syringe to express the reactive components of the multi-part biomedical composition in a second blended or mixing ratio to form a coating having physiologically distinct layers.

The present invention, in yet another embodiment, relates to a device for uninterruptible simultaneous expression of a multi-part biomedical composition in a step-wise changing ratios, which comprises at least three chambers fixedly arranged together within an optional holder, each chamber having a spray pump and each chamber separately containing flowable components of the multi-part biomedical composition. Each spray pump has an actuator positioned in proximity to said spray pump, with all actuators fixedly arranged together. The device further comprises at least one lever releasably restraining at least one actuator from actuating at least one spray pump.

The present invention, in still further embodiment, relates to a device for uninterruptible simultaneous expression of a multi-part biomedical composition in varying mixing ratios comprising a first syringe, a second syringe and a third syringe. Each syringe has proximal end and an opposing distal end, and each syringe contains a reactive component of the multi-part biomedical composition, with syringes comprising a barrel and elongated rods, the rods having a front end and an opposing rear end and a piston attached to each of said rods at the front end. The pistons of the first and the second syringes are positioned at the distal end and the piston of the third syringe is located between the distal end and the proximal end. The rods of the first and the second syringes are attached at the rear end to a bar for simultaneous movement and the rod of the third syringe is not attached to said bar, forming a gap between the rear end of the rod of the third syringe and the bar. The bar projects over said rod of the third syringe.

BRIEF DESCRIPTION OF THE FIGURES

FIGS. 8A-D show embodiments of the present invention.
FIG. 11 shows embodiment of the present invention.
FIGS. 15A-C show embodiments of the present invention.
FIGS. 17A-B show embodiments of the present invention.

DETAILED DESCRIPTION OF THE INVENTION

The present invention relates to biomedical coatings, including sealing agents, adhesives, hemostatic agents, and adhesion preventing coatings, more specifically to compositions and devices to deliver such coatings, whereby the composition of the coating and properties of the coating are variable across the thickness of the coating. The present invention also relates to delivering biomedical coatings, including sealing agents, adhesives, hemostatic agents, and adhesion preventing coatings, from a single applicator in which the medical professional selects the composition and function desired at the time of delivery to a work surface of a given tissue site. The present invention further relates to delivering biomedical coatings, whereby the composition and function automatically changes during the delivery to a work surface of the given tissue site.

The present invention relates to an applicator and method of applying a biologic fluid agent comprising multiple fluid components to a work surface, and is particularly, although not exclusively, useful for applying biologic sealants, or other biologic fluid agents, to biological tissue to effect hemostasis, close wounds, apply skin grafts or achieve other desirable therapeutic results. More particularly, the invention relates to application of a multiple-component tissue sealant agent, one component of which comprises a polymerizable biological or synthetic sealant agent, for example fibrinogen, and the other component of which comprises a biologically acceptable polymerization catalyst or activator agent, for example, thrombin. Other polymerizable and activation agents may be used, as is understood by those skilled in the art.

The present invention provides a surgeon or other user of a handheld biologic or synthetic fluid agent applicator with more flexibility, for example the ability to deliver an agent through a variable output biologic fluid agent applicator whereby the mixing ratio of components forming the agent changes automatically or manually by choice of user during the application, resulting in one composition forming a tissue-facing side of the coating, and another composition forming an opposing side of the coating.

An end result of the inventions described herein is an ability to increase the flexibility physicians need to deal with incised or otherwise traumatized bodily tissues having a variety of clinical needs. After a procedure on an internal organ, a physician primarily needs to close the incisions created. A secondary, but important, need is to prevent any intermittent or continuous leakage of fluids such as blood, or in the case of lung tissue, air. A third need is to prevent or at least minimize unwanted surgical adhesion formation that often takes place between bodily tissues post-operatively. These three different clinical needs have not yet been addressed by a single material or procedure.

This disclosure will make available a hydrogel system and means of delivering this system to simultaneously achieve advantageous properties that can address multiple clinical needs as described above. Methods will be disclosed to allow the formation of hydrogels that can multifunction as a surgical adhesive and/or sealant and will also have excellent surgical adhesion preventative properties or other supplementary properties. This disclosure describes hydrogel systems and devices to deliver hydrogel precursors providing a compositional variation to address those different clinical needs. In some embodiments, this compositional variation can be a gradient orthogonal to the surface of the bodily tissue; i.e. a hydrogel which changes in composition, and thus in properties, as a function of the distance away from the tissue upon which it is applied. In other embodiments, this compositional variation is effected in a step-wise fashion, whereby part of the coating applied has a first composition, and the coating applied on top has a second composition, with the first and second compositions differ only in mixing ratio of the composition forming pre-cursors. The precursor components of the hydrogel system of choice are typically water soluble (before application), and are capable of curing, usually by cross-linking. It is a further objective of this disclosure to provide different degrees of cross-linking on demand; in a preferred application, the formed hydrogel is absorbable.

During a surgical procedure, incisions are created to access the sites of interest. Once the intended objectives are achieved, these incisions are closed for healing. In many cases, these incisions or wounds caused by trauma are closed with sutures or staples. Surgical adhesives also have been used more and more often in the past decade for closing external incisions. Recently, a surgical adhesive focus has been in the area of absorbable adhesives, potentially enabling their use for internal incisions. Hydrogels containing PEG (polyethylene glycol) moieties are of particular interest. Multi-armed PEGs are examples of these hydrogel components.

However, internal incisions require more than just a closure for healing. Examples include the anastomosis of a tubular structure having a lumen requires not only the re-joining of tissue, but also leakage prevention of the lumen content. In these cases, a surgical sealant is required to seal the joint to prevent the leakage of lumen content. Moreover, at the interface between the incised tissue or organ and adjacent tissues or organs, surgical adhesions can occur due to biological responses. To prevent unwanted surgical adhesion formation, several options are currently available. One is the use of anti-inflammatory agents; another approach is the use of a barrier. Barrier materials used as adhesion preventative devices include oxidized regenerated cellulose (ORC) and polyethylene glycol (PEG) derivatives. Presently a surgeon can select a product that functions primarily in one of the four performance categories: adhesive, sealant, adhesion barrier, or hemostat. An object of this invention is to conveniently provide a single product that imparts two or more of these functions and to provide a convenient method to allow the surgeon to select the product characteristics at the time of application.

It is a further aspect of this invention to provide an applicator system that is capable of applying components to result in a hydrogel in which there exists a gradient of properties. That is, properties of the hydrogel portion closest to the surface of the bodily tissue may, for instance, function as a surgical adhesive or a surgical sealant (achieved for instance by having a high cross-link density) or hemostat. As one moves further from the surface, the properties of the hydrogel change (achieved for instance by having a lower cross-link density) allowing the surface portion to exhibit adhesion barrier characteristics or other different properties. Thus in one aspect of the subject invention, a hydrogel is provided in which there is gradient of cross-link density or step-wise change in cross-link density as one moves orthogonally from the surface of the bodily tissue. These changes in cross-link density will result in a gradient of properties as one moves orthogonally from the surface of the bodily tissue.

To be clear, this invention, in one aspect, is directed towards the delivery of known materials (fibrinogen/thrombin or PEGs or other multiple components hydrogels) discussed in the patent or open literature or commercially available are commonly provided as a material with one pre-determined property to address one type of clinical need, for instance as either a surgical adhesive or as a surgical sealant or as a surgical adhesion barrier, or as a hemostat, respectively.

It is an object of this disclosure to provide the surgeon with a single device that has the flexibility to conveniently deal with a number of clinical needs of bodily tissues. To achieve this objective, methods will be disclosed to allow the formation of materials (particularly fibrinogen/thrombin combinations and hydrogels) that can optionally function as a hemostat, and/or a surgical adhesive, and/or a surgical sealant, and/or will have excellent surgical adhesion preventative properties, with at least two of the above characteristics present, as selected by the surgeon at the time of the delivery of the coating components, that is at the time of the surgical application.

In one embodiment of the present invention the use of polyethylene glycol (PEG) derivatives, particularly multi-armed functionalized hydrogel precursors is contemplated. In one such case, an aqueous solution of a multi-armed PEG tipped with very reactive esters groups [e.g. based on N-hydroxy succinamide leaving groups] are reacted with an aqueous solution of multi-function amines [e.g. lysine or a multi-armed PEG tipped with amines], to form biomedical coatings of the present invention.

In the above case, the characteristics of the final product are controlled by the initial concentrations of the two solutions, and their relative mix rations. For instance, if one views the lysine solution as a cross-linker, it will be easy to see that the relative amount of this component employed will alter the crosslink density of the hydrogel so formed, and thus its characteristics. With a relatively low cross-link density, the resulting hydrogel is better suited as an adhesion preventative. With increased cross-link density, the hydrogel that is formed is less swellable and possesses higher mechanical properties. As cross-link density increases, the resultant hydrogel can function as a sealant; at still higher cross-link densities, the mechanical properties are such so as to allow its use as an adhesive.

Figure 1A:
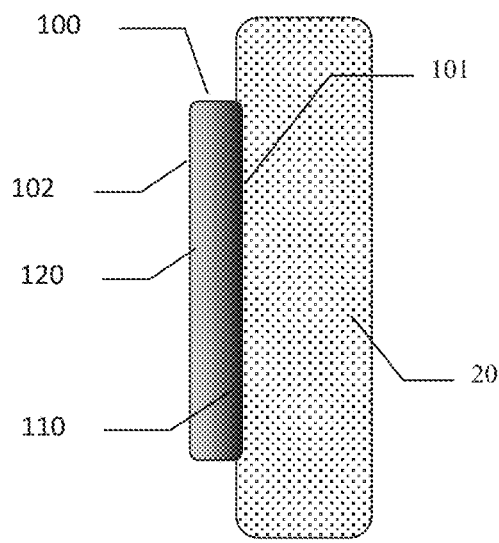
FIG. 1A shows a coating resulting from a gradual change in the mixing ratio of the coating components.

Referring now to FIG. 1A, representing a schematic cross-sectional view of one embodiment of the present invention, coating 100 on tissue 20 has a tissue facing surface 101 and an opposing surface 102. Coating 100 forming in situ on tissue 20 has a mixing ratio of components gradually changing, for example from high cross-linker percentage to low cross-linker percentage, resulting in high crosslinker concentration area 110 on tissue 20 surface and low crosslinker concentration area 120 adjacent to opposing surface 102. The gradual change is schematically indicated in FIG. 1 by a shading gradient.

Figure 1B:
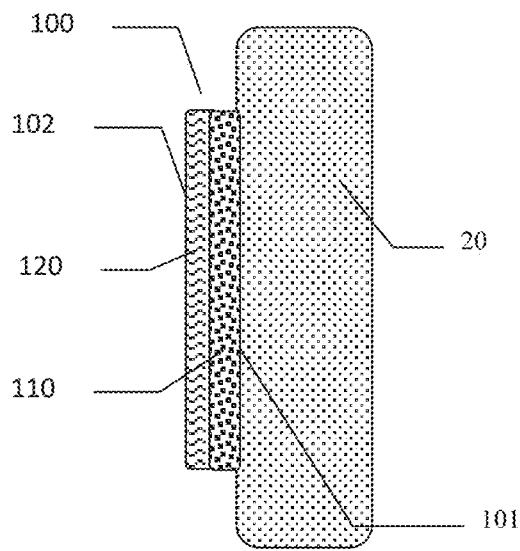
FIG. 1B shows a coating resulting from a step-wise change in the mixing ratio of the coating components.

Referring now to FIG. 1B, representing a schematic cross-sectional view, according to another embodiment of the present invention, coating 100 has a mixing ratio of components changing step-wise, for example from high cross-linker percentage to low cross-linker percentage, resulting in layer 110 with high crosslinker concentration, facing tissue 20 surface and adjacent to tissue facing surface 101, step-wise changing to layer 120 with low crosslinker concentration adjacent to opposing surface 102 of coating 100. Layers 110 and 120 are physically distinct layers in a sense that the composition of the layers is different. Layers 110 and 120 are physiologically distinct in a sense that their interaction with tissue is different due to different properties of the layers formed by mixing components in different mixing ratios.

Figure 2A:
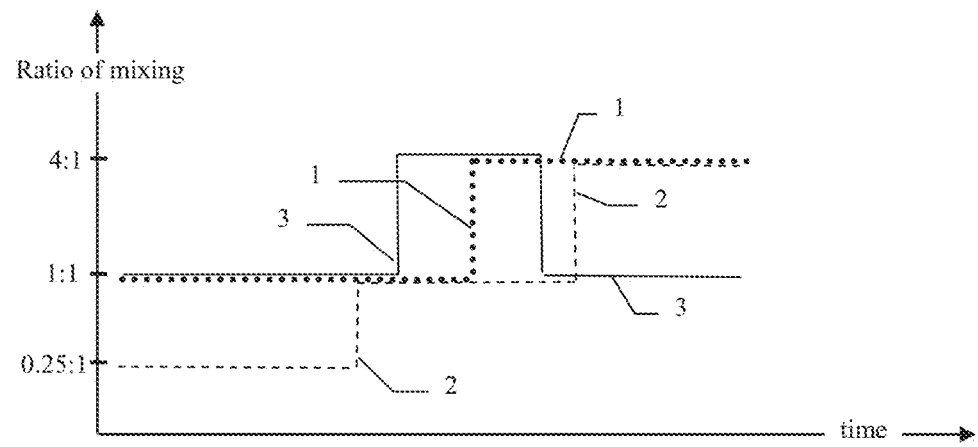
FIG. 2A shows a schematic chart representing several scenarios of changing ratio of mixing of two components during the time of the delivery of the coating.

Referring now to FIG. 2A, examples of ratios of mixing upon expressing the two-part composition are shown in a format of a schematic chart representing the ratio of mixing of two components relative to coating delivery time or relative to distance from tissue surface. From a practical viewpoint, this corresponds to the time of expressing the mixture from a delivery device, as the initially expressed mixture will generally lie closest to the tissue surface, while later expressed material may lie upon the first applied layer. It is also to be understood that in some instances, one may choose to express the later mixture not only on the previous layer but also upon virgin (uncoated) tissue areas. The chart presented in FIG. 2A, which is not drawn to scale, shows three exemplary mixing ratios of components, including ratio 0.25:1; ratio 1:1; and ratio 4:1 which are step-wise changing as expression from the delivery device progresses. Line 1 shows the mixing ratio changing step-wise from about 1:1 to about 4:1. Line 2 shows the mixing ratio changing step-wise from 0.25:1 to 1:1 and then to 4:1. Line 3 shows the mixing ratio changing step-wise from about 1:1 to about 4:1 and then back to 1:1. To be clear, a gradual change in the mixing ratio is also within the scope of this invention as described previously.

Figure 2B:
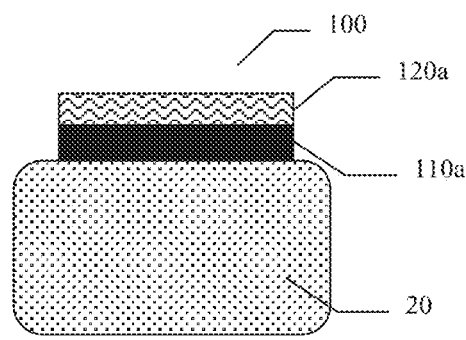
FIG. 2B shows, a coating formed on tissue corresponding to the scenario of Line 1 of FIG. 2A.
Figure 2C:
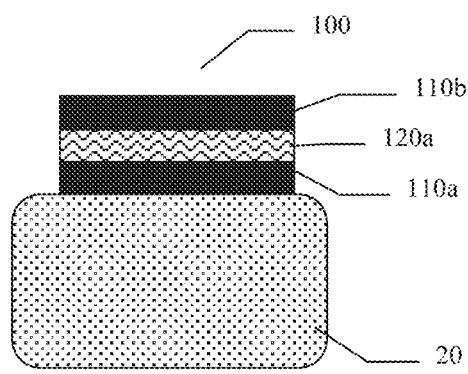
FIG. 2C shows, a coating formed on tissue corresponding to the scenario of Line 3 of FIG. 2A.

Referring now to FIG. 2B, coating 100, formed corresponding to the scenario of Line 1 of FIG. 2A, is schematically shown on tissue 20, comprising a layer 110*a* formed on tissue 20 from mixture of 1:1 ratio and layer 120*a* formed from mixture with 4:1 ratio on top of layer 110*a*. Referring now to FIG. 2C, coating 100, formed corresponding to the scenario of Line 3 of FIG. 2A, is schematically shown, comprising layer 110*a* formed on tissue 20 from mixture of 1:1 ratio, layer 120*a* formed from mixture of 4:1 ratio on top of layer 110*a*, and layer 110*b*, formed from mixture of 1:1 ratio on top of layer 120*a*. Other mixing ratio scenarios are possible and will be easily apparent to these skilled in the art.

According to one embodiment of the present invention, coating 100 is obtained by altering the volume ratio (fraction) of the components of the coating during application, while maintaining a constant total volumetric throughput or allowing the total volumetric throughput to change during application. In one embodiment, the ratio of the component streams changes, e.g. instead of constantly combining a feed stream of 50% of solution A with 50% of solution B, coating 100 is initially applied by a feed stream of 50% of solution A with 50% of solution B, and then changes the feed stream (continuously or abruptly) to a feed stream of 30% of solution A with 70% of solution B. This change can be achieved by maintaining a constant total volumetric throughput or by allowing the volumetric throughput to change during application. In the first case, if a total volumetric throughput of 0.2 ml/sec is delivered at the start of the application, the same total volumetric throughput of 0.2 ml/sec will be delivered at the second stage of the application, but at a different AB mix ratio.

According to another embodiment of the present invention, the supply rate decreases (or increases) for one of the components; the component volume ratio (fraction) is altered, as will the total volumetric throughput.

Figure 3:
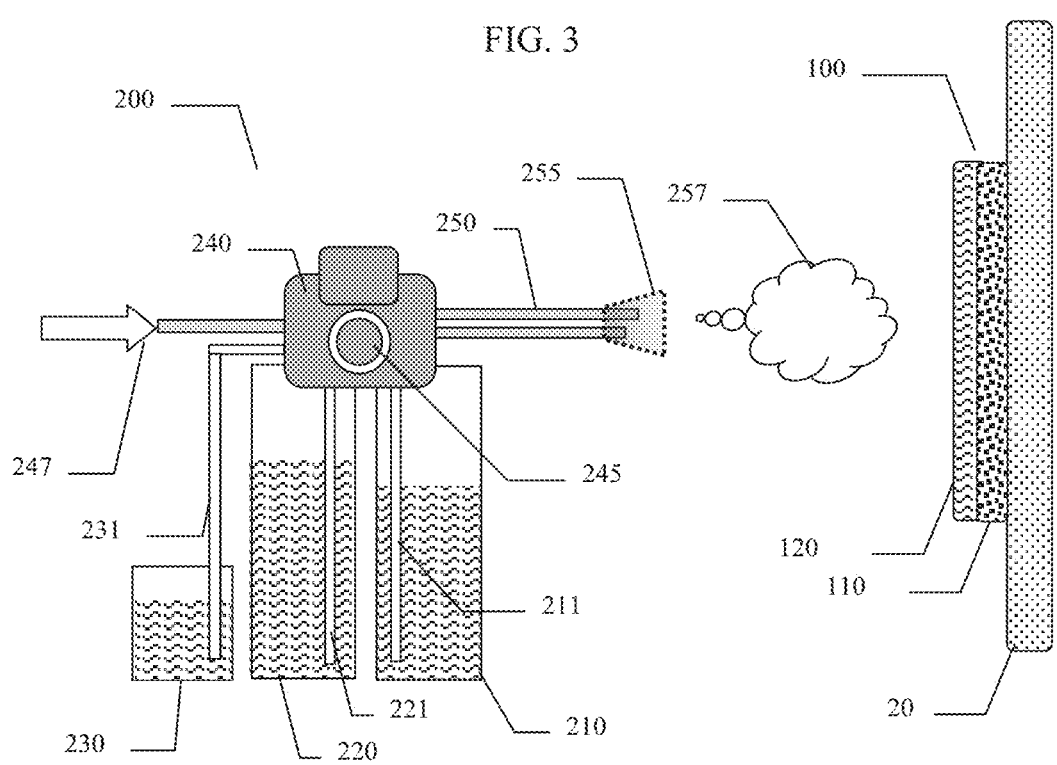
FIG. 3 shows a schematic of a dispenser with the means of changing the mixing ratio of components.

Various designs to regulate the volume during dispensing are contemplated and will be discussed in more detail. Referring now to FIG. 3, schematically showing one embodiment of the present invention, delivery device 200 comprises component A container 210, component B container 220, and optional component C container 230, inlet tubes 211, 221, 231, manifold 240 having means 245 to change the mixing ratio, optional pressurized air inlet 247, outlet tubes 250 terminating with optional mixing nozzle 255 and ejecting liquid non-cross-linked components schematically shown as stream 257 towards tissue 20 and forming coating 100. Component A can be a cross-linkable polymer, component B can be a cross-linker, and optional component C can be a diluent (such as water or other non-cross-linkable material, such as non-functionalized PEG, gelatin solution, protein solution, or similar). In application, means 245, such as valve, changes the expression of the component mixture after a portion of coating 100 has been applied to tissue 20, forming layers 110 and 120 on tissue 20.

Table 1 shows, for illustration purposes, exemplary volume ratios of a three-component multi-part biomedical composition forming the coating of the present invention. In one embodiment, the initial mixing ratio corresponds to case 1, i.e. with components A and B delivered in ratio 1:1 and no component C for the overall mixing ratio 1:1:0. The expression can then change to case 2, with decrease in component B and addition of component C, with A:B:C ratio of 1:0.5:0.5. Alternatively, the expression can change from case 1 to case 3, with the same expression of components A and B, and addition of component C in equal volume, with A:B:C ratio of 1:1:1. In yet another scenario, the expression changes from case 1 to case 4, with the same volumetric expression of component A, no expression of component B, and addition of component C in equal volume, with A:B:C ratio of 1:0:1.

TABLE 1

Exemplary Volume Ratios of a Three-Component Coating of the Present Invention

| Case | Component A | Component B | Component C |
|---|---|---|---|
| 1 | 1 | 1 | 0 |
| 2 | 1 | 0.5 | 0.5 |
| 3 | 1 | 1 | 1 |
| 4 | 1 | 0 | 1 |

According to another embodiment of the present invention, there is provided a dual chamber for holding components A and B separately and a spray head to regulate their supply. This design can, abruptly (step-wise) or continuously, change the supply of one of the components on demand by the user. A gear pressing against the supply of component B can be used to regulate/control the volume delivered to the nozzle. A further refinement of this embodiment allows the control gear to be set at a plurality of levels, providing additional control to the surgeon. This leads to different degree of reaction therefore different properties to address different clinical needs. Instead of a gear mechanism, a bladder can also be used to regulate/control the delivery volume.

According to yet another embodiment of the present invention, the concentration of one or all components can be altered. In this embodiment, delivery device will have triple chambers for holding component A, B, and C (the diluent) and a spray head to regulate the supply of component C (diluent). This design also allows abruptly changing the supply on demand by the user. The control regulates the supply of diluent starting from "complete off" to "open at multiple levels". The diluent is to merge with at least one of the reactive component first to ensure the dilution of this component before mixing with the other reactive component. Alternately, the diluent stream may be added during the spraying process to allow mixing at the droplet level. The potential candidates for a diluent are either a solvent for the materials (most likely water in this case) or a less reactive component.

According to still another embodiment of the present invention, one component can be changed to a less reactive component. In this embodiment, component A is first delivered in a mixture with component B, then switching to delivery of component A in mixture with component C. A multiple-chambers bottle, connected to an adaptor, and then connected to a spray head can be utilized as a delivery device. An adaptor can serve as a toggle switch to change the connection of different components to one channel of the spread nozzle. The other nozzle may be connected to one constant component.

Figure 4A:
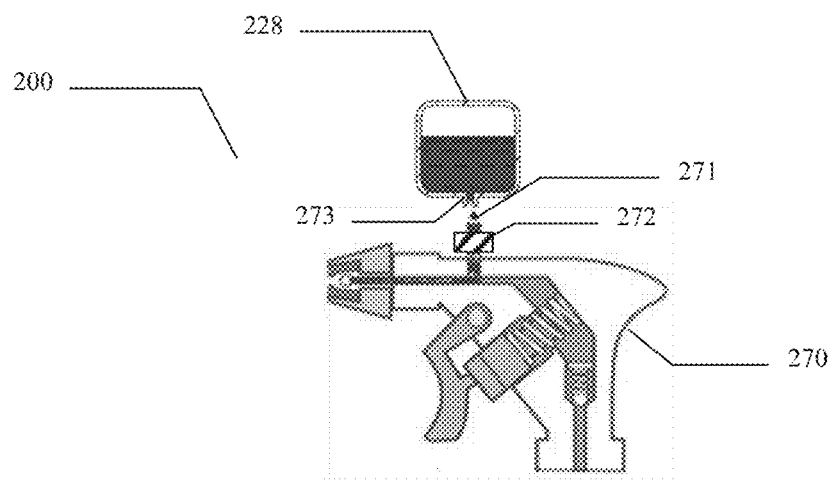
FIG. 4A shows a schematic of a dispenser with the means of changing the mixing ratio of components.

According to still another embodiment of the present invention, as schematically illustrated in FIG. 4A, component A sprayer 270 has a feature to introduce component B. Piercing stem 271 connects container 228 with component B to sprayer 270 with a pierceable cap 273. Valve 272, which controls the mixing ratio, is installed on piercing stem 271 with the Venturi effect ensuing component B intake. For different clinical needs, container 228 is then removed and another one containing different component (such as component C) is connected. In an additional embodiment, container 228 can have multiple chambers, which can be connected to sprayer 270 through an adapter (not shown) that can switch the connection between the different chambers.

Figure 4B:
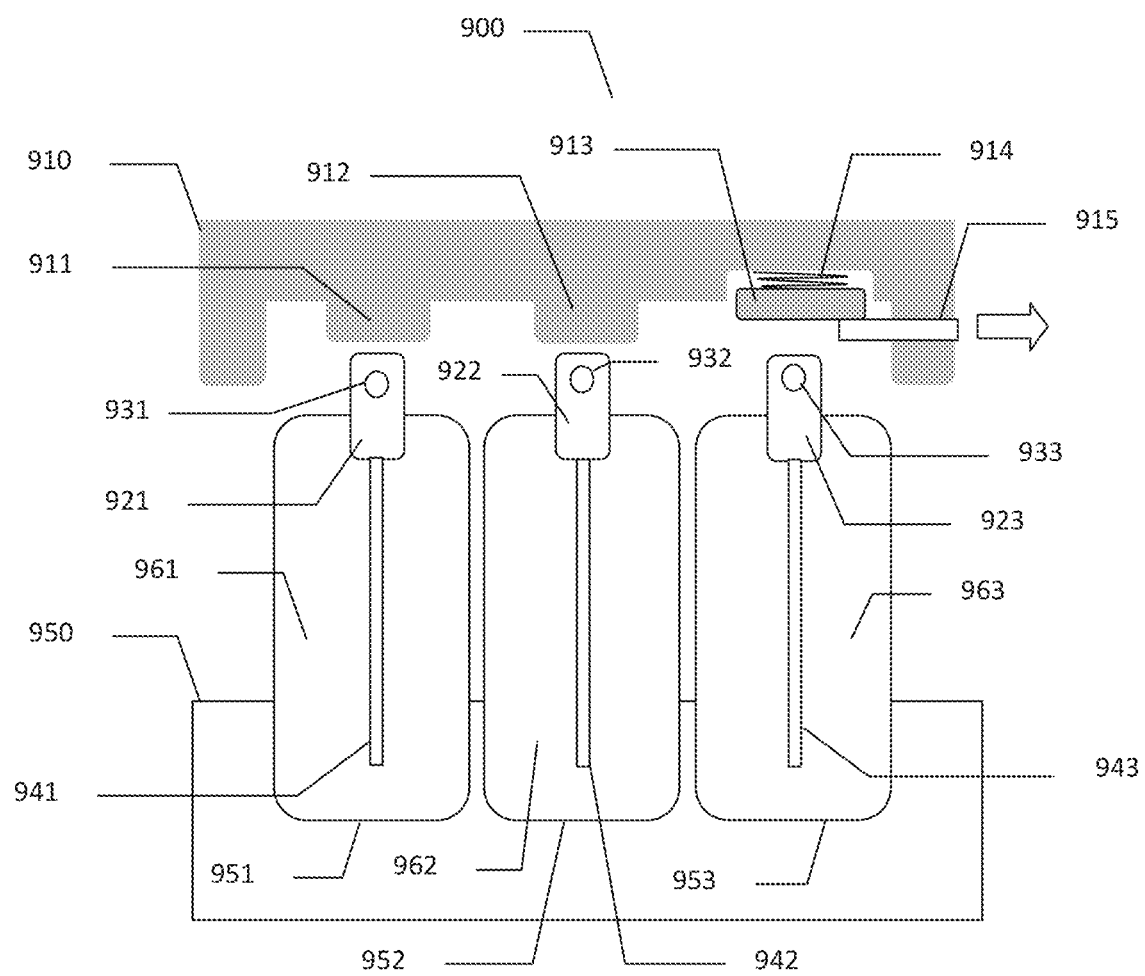
FIG. 4B shows one embodiment of the inventive multi-component applicator illustrating the ability to select the mixing ratio of the different components during application.

FIG. 4B shows yet another embodiment of the present invention, with delivery device 900 with actuator assembly 910, containing actuators 911, 912, and 913 removably connected to multiple spray pumps, 921, 922, and 923, which are connected to multiple chambers, 951, 952, and 953 arranged within optional holder 950, with chambers separately containing flowable components 961, 962, and 963. Nozzles 931, 932, and 933 are provided on spray pumps with feed tubes 941, 942, and 943 submerged under liquid level in chambers and connected to pumps. Actuators 911, 912, and 913 depressing or actuating spray pumps 921, 922, and 923 result in spraying of flowable components 961, 962, and 963 through nozzles 931, 932, and 933 with flowable components 961, 962, and 963 supplied via feed tubes 941, 942, and 943. Lever 915 releasably restrains actuator 913 in the actuator assembly 910. When lever 915 is pulled to release the actuator 913, as shown schematically by an arrow, spring 914 pushes the actuator 913 to the same level as actuators 911 and 912. At this time, lever 915 reengages and locks actuator 913 in place. This locking mechanism allows all actuators to engage the pumps at the same time to express flowable components 961, 962, and 963. This locking process is reversible and thus allows the users to change the mixing ratio at any time as needed. Additionally, lever 915 can be set at unlock position leading to a continuous variation of component 963.

In operation, container 951 is filled with component 961, such as a crosslinker; container 952 is filled with component 962, such as a crosslinkable prepolymer; container 953 is filled with component 963, such as a diluent to change the ratio between crosslinkable prepolymer and crosslinker, which can be another crosslinkable prepolymer or water. When actuator assembly 910 is depressed to engage the pumps, pistons 911 and 912 activate pumps 921 and 922 to express components 961 and 962 via nozzles 931 and 932. After the lever 915 is pulled to release and relock actuator 913 in a new position, pump 923 will also be activated when piston assembly 910 is depressed thus changing the mix ratio.

Figure 4C:
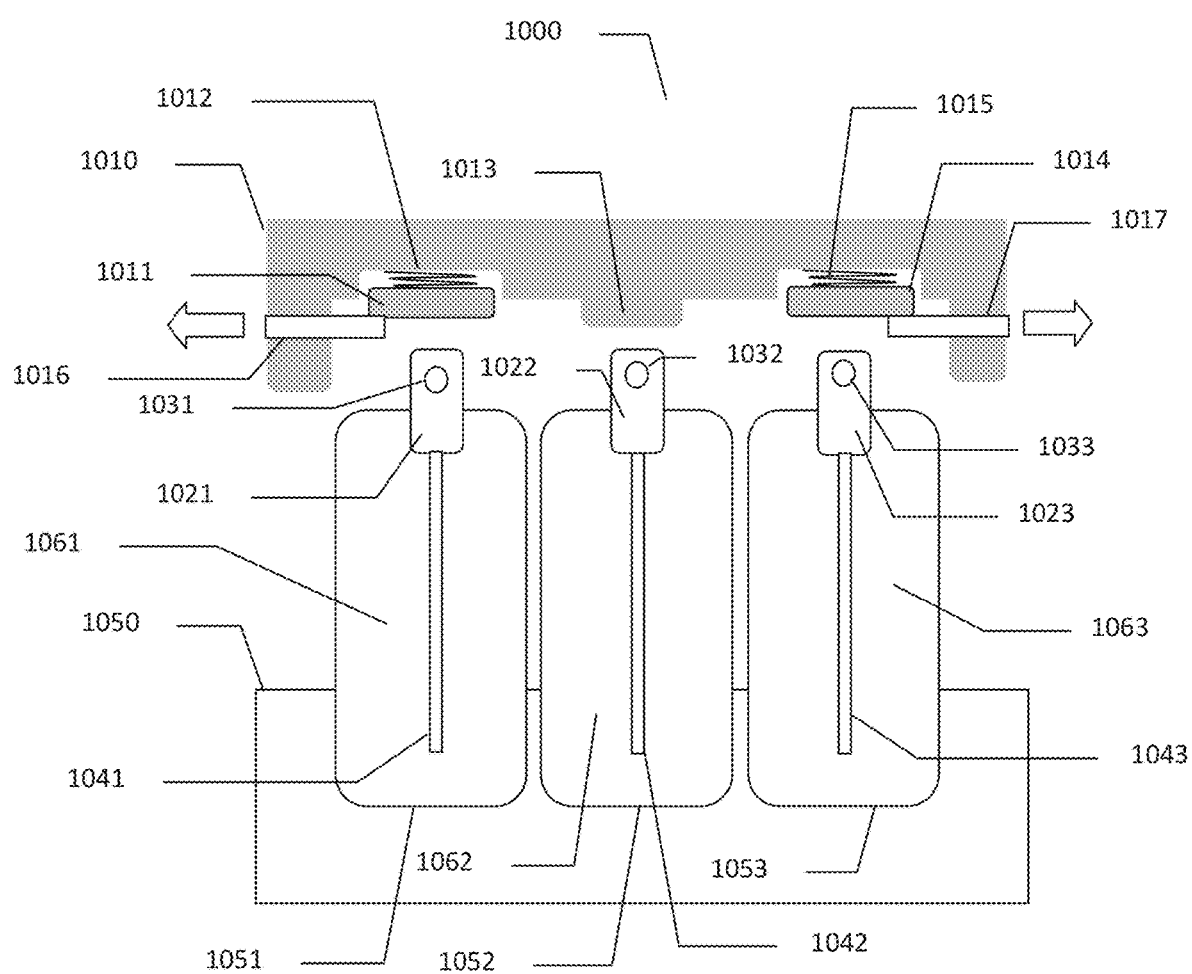
FIG. 4C shows an alternate embodiment of the inventive multi-component applicator illustrating the ability to select the mixing ratio of the different components during application.

FIG. 4C shows another embodiment, with delivery device 1000 having a piston assembly 1010, containing actuators 1011, 1013, and 1014 engageably connected to spray pumps 1021, 1022, and 1023 attached to chambers 1051, 1052, and 1053 arranged within optional holder 1050, with chambers separately containing flowable components 1061, 1062, and 1063. Nozzles 1031, 1032, and 1033 are provided on spray pumps with feed tubes 1041, 1042, and 1043 submerged under liquid level in chambers and connected to pumps. Levers 1016 and 1017 initially restrain actuators 1011 and 1013 in actuator assembly 1010. When the levers 1016 and 1017 are pulled as shown by arrows to release actuators 1011 and 1014, springs 1012 and 1015 will push actuators 1011 and 1014 to the same level as actuator 1013. At this time levers 1016 and 1017 will reengage and lock actuators 1011 and 1014 in place. This allows all pistons to engage all pumps at the same time to express components from each pump. In certain applications, actuators 1011 and 1014 can be engaged separately. This process is reversible thus allows the users to change the mixing ratio at any time as needed.

In operation, container 1051 is filled with component 961, such as a crosslinker, and container 1052 is filled with component 962, such as a crosslinkable prepolymer, and the container 1053 is filled with component 963, such as an alternative crosslinker. By choosing to activate either actuator 1011 or 1014 or both will achieve different ratio between crosslinkable prepolymer and crosslinker.

According to further embodiments of the present invention a two-part adhesive (or sealant) coating composition (such as a PEG-based multi-arm macromer with ester functionality and multi-arm crosslinker with amine functionality) is mixed in a variable ratio in situ to result in a coating with highly adhesive/sealing properties (high concentration of cross-linker) at the tissue contacting surface of the coating, step-wise or continuously changing to non-adhesive, adhesion-preventive properties (low concentration of crosslinker) at the opposite surface of the coating. The composition is delivered uninterruptedly from a single applicator delivery device (having two chambers for storing two-part composition) and two separate discharge nozzles (or a single mixing discharge nozzle), providing a continuous change in the mixing ratio, resulting in a compositional gradient orthogonal to the tissue interface or step-wise compositional change at a plane parallel to the tissue interface. The delivery device has control means for continuously or step-wise changing the mixing ratio. The delivery device has an optional third chamber containing either diluent or a weaker crosslinker.

According to further embodiments of the present invention, there are provided methods and delivery devices for forming bi-layer or multi-layer coatings using variable mixing ratios of two-part compositions. Briefly, in one embodiment, a two-part coating or sealant or hemostatic composition is applied from a delivery device whereby the mixing ratio of two components of the coating changes step-wise from one ratio to another ratio during the expression, resulting in the first layer of the coating having one composition (e.g. hemostatic), and second layer of the coating having another composition (e.g. sealant and/or anti-adhesion). The mixing ratio changes due to changing of the relative expression rate of one component relative to another, i.e. first component is expressed at one rate, then switches to a faster or slower rate. Thus the delivery device provides automatic switch from one mixing ratio to another mixing ratio as expression progresses.

The delivery devices of the present invention automatically and uninterruptedly switch from the first mixing ratio to the second mixing ratio as the expression progresses with no additional user input resulting in bi-layer or tri-layer coatings.

Non-limiting examples of two-part adhesives (or sealants) are:
a) Fibrinogen:thrombin in variable ratios such as about 1:1 switching during applying the coating to ratio of about 5:1 or vice versa. Other ratios are changing from 1:1 to 1:2; 1:1 to 10:1, and similar. The switching can occur, for example, half-way during applying of the coating.
b) PEG-based multi-arm macromer with ester functionality and multi-arm crosslinker with amine functionality) which is mixed in a variable ratio to result in a coating with highly adhesive/sealing properties (high concentration of cross-linker) at the tissue contacting surface of the coating, then step-wise automatically changing to non-adhesive, adhesion-preventive properties (low concentration of cross-linker) at the opposite surface of the coating.
c) Any cross-linking agent and polymerizable monomer.
d) Polymeric coating and a diluent.

Generally, switching can occur at any time during coating delivery, such as after delivering 10%; 20%, 30%, 50%; 75%, 90% of the coating material. Preferably switching form one ratio to another occurs after delivering about 30%, 50%; or 70% of the coating material. There can be an optional pause of several seconds before starting delivering of the second mixing ratio.

According to an embodiment of the present invention, the composition is delivered uninterruptedly from a single delivery device (having at least two syringes for storing the two-part composition) and at least two separate discharge nozzles (or a single mixing discharge nozzle). At least one of the syringes changes the component expression rate during expression. According to embodiments of the present invention, at least one syringe of a dual syringe delivery device has two diameters; a piston engaged with a ring-shaped gasket is used to express component from large diameter compartment and the same piston disengaged from the gasket is used to express component from the small diameter compartment. The gasket engages/disengages at the border between large diameter and small diameter compartments as the piston pushed by a user progresses through the syringe.

Figure 5A:
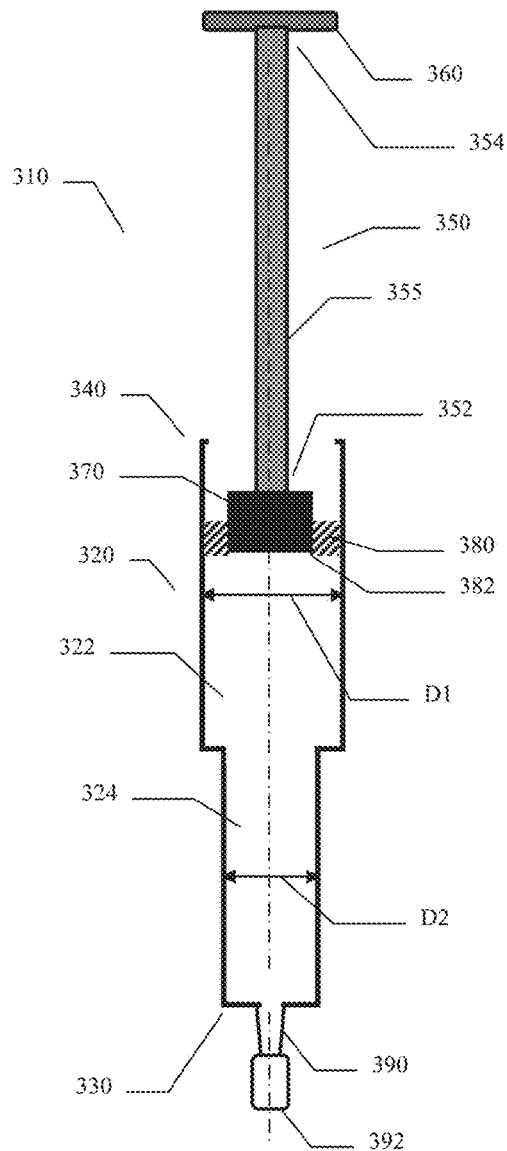
FIGS. 5A-C show embodiments of the present invention.

Referring now to FIG. 5A, a schematic cross-sectional view of an embodiment of a first syringe 310 of multi-syringe delivery device 300 (not shown in FIG. 5) is presented. First syringe 310 comprises a generally tubular hollow barrel 320 extending along an axis and having a proximal end 330 and an opposing distal end 340 spaced axially behind proximal end 330. Barrel 320 comprises a first retention compartment or large diameter compartment 322 having internal diameter D1 and positioned closer to distal end 340 and a second retention compartment or small diameter compartment 324 having internal diameter D2 and positioned closer to proximal end 330, both compartments 322 and 324 spaced axially and shaped as hollow cylinders, with larger diameter D1 at least 10% larger than smaller diameter D2. An elongated plunger 350 projects axially rearward out of distal end 340 of barrel 320 and moveable axially in barrel 320 from distal end 340 to proximal end 330. Plunger 350 has a front end 352 and an opposing rear end 354, and comprises an elongated rod 355, with optional handle 360 mounted at the rear end 354 on rod 355, with piston 370 mounted at the front end 352 on rod 355. Piston 370 has substantially cylindrical shape, and has a diameter closely matching diameter D2 for tight but slidable fit inside small diameter compartment 324. Ring-shaped or hollow cylinder shaped gasket 380 with an optional barb or lip 382, has outside diameter closely matching diameter D1 for tight but slidable fit inside large diameter compartment 322, and inside diameter closely matching diameter D2 so that piston 370 can tightly but slidably fit inside gasket 380. Nozzle 390, which is located on proximal end 330 of barrel 320, expresses component A from first syringe 310 and can optionally be capped by a removable cap 392.

FIG. 5A shows the first syringe 310 prior to expressing component A, or during expressing component A from large diameter compartment 322 by advancing plunger 350 towards proximal end 330, but with piston 370 remaining within large diameter compartment 322, corresponding to high volumetric expression rate from first syringe 310.

Figure 5B:
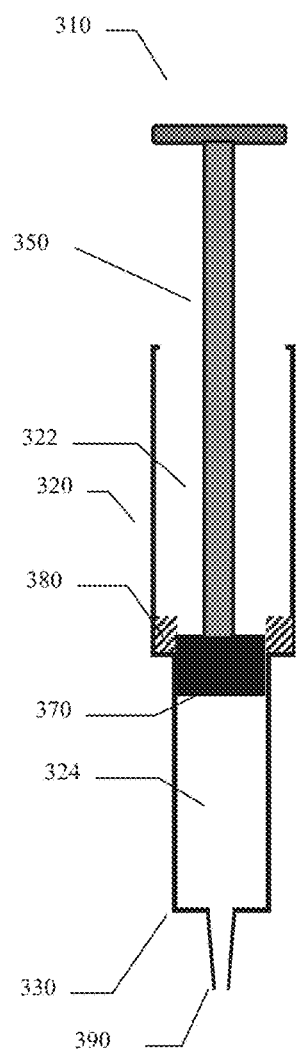
Figure 5C:
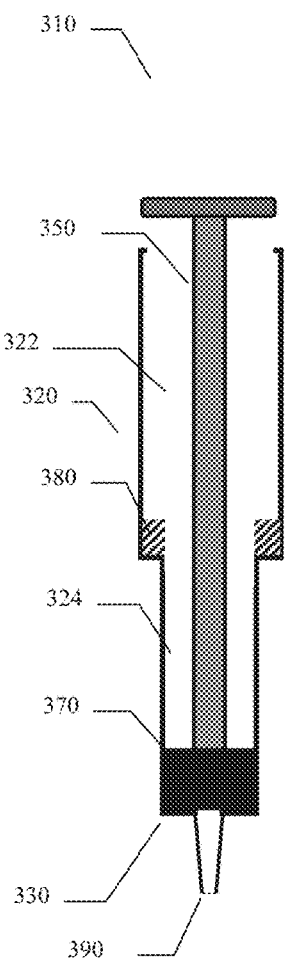

Gasket 380 always remains within large diameter compartment 322. In operation, piston 370 engaged as shown with gasket 380 and held in engaged position by optional barb or lip 382 advances through large diameter compartment 322 towards proximal end 330 or towards nozzle 390, expressing component A through nozzle 390 at a high volumetric expression rate. As piston 370 engaged with gasket 380 reaches small diameter compartment 324, gasket 380 remains in large diameter compartment 322 and disengages from piston 370, while piston 370 driven by plunger 350 continues advancing into small diameter compartment 324. Referring now to FIG. 5B, first syringe 310 is shown in further operation, after expressing component A from large diameter compartment 322 and beginning expression from small diameter compartment 324, corresponding to low volumetric expression rate from first syringe 310. As can be seen from FIG. 5B, as piston 370 driven by plunger 350 has advanced into small diameter compartment 324, gasket 380 cannot advance into small diameter compartment 324 and remains in large diameter compartment 322. As piston 370 advances within small diameter compartment 324, volumetric expression rate from first syringe 310 will decrease, provided that the linear speed of advancing plunger 350 remains the same. Referring now to FIG. 5C, first syringe 310 is shown upon completion of the expression of component A with piston 370 stopped at proximal end 330 of barrel 320.

Upon change from expressing from large diameter compartment 322 to expressing from small diameter compartment 324, the rate of component expression will change proportionally to the square ratio of diameters D1 to D2, if the linear speed of advancing plunger 350 remains the same. If plunger advances within a cylindrical body at a linear speed S, the volumetric expression rate V will be a function of diameter D:

$$V = S\pi \frac{D^2}{4}$$

If plunger advances at a speed S=0.5 cm per second and D1=1.5 cm and D2=1.0 cm, the volumetric expression rate will be for large diameter compartment 322, $V_1$=0.88 ml/s and for small diameter compartment 324: $V_2$=0.39 ml/s, resulting in changing expression rate by 2.25 times. If plunger advances at a speed S=1 cm per second and D1=2 cm and D2=1 cm, the volumetric expression rate will be for large diameter compartment 322: $V_1$=3.14 ml/s and for small diameter compartment 324: $V_2$=0.785 ml/s, resulting in changing expression rate by 4 times. As shown above, FIG. 5A shows position corresponding to higher expression rate of component A from first syringe 310 and FIG. 5B shows position corresponding to lower expression rate of component A from first syringe 310.

Figure 6A:
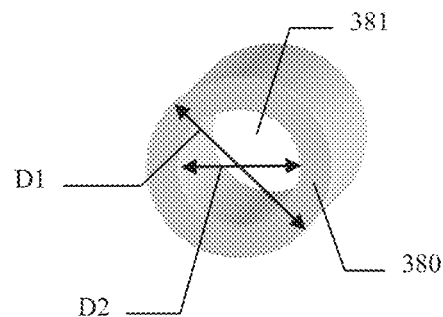
FIGS. 6A-E show embodiments of the present invention.
Figure 6B:
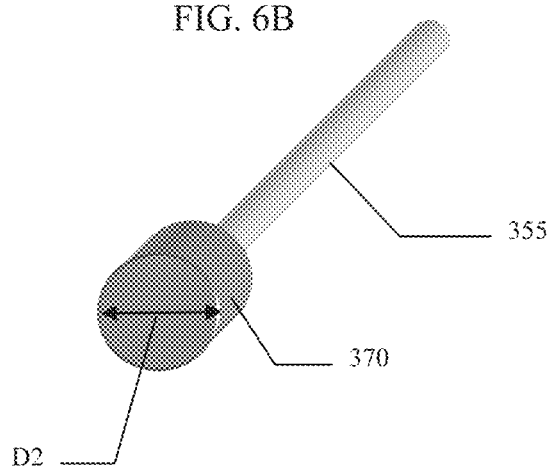
Figure 6C:
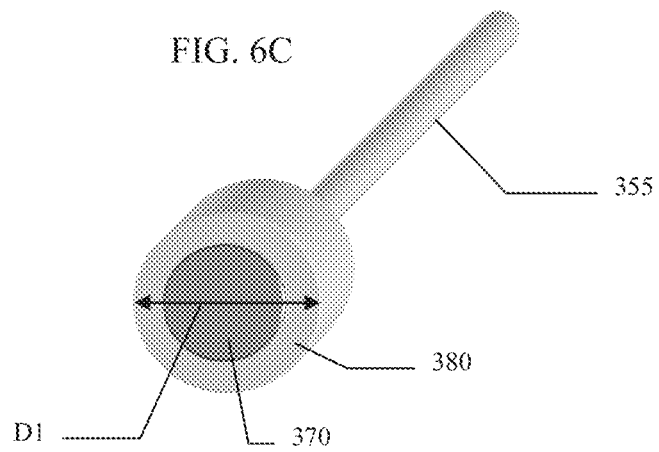
Figure 6D:
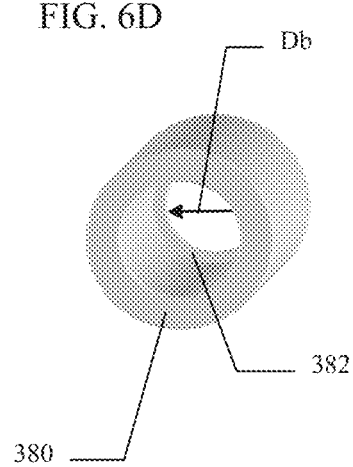
Figure 6E:
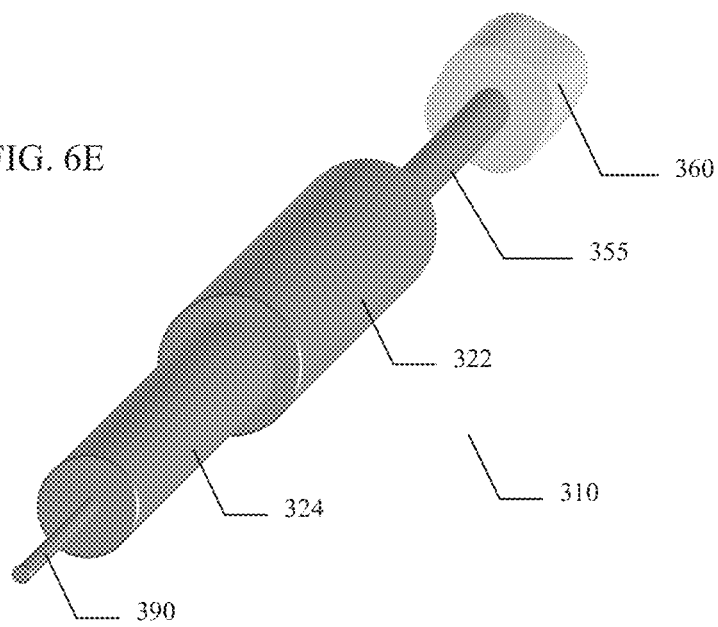

Referring now to FIGS. 6A-E, FIG. 6A shows gasket 380 with external diameter matching diameter D1 and with gasket opening 381 having diameter matching diameter D2; FIG. 6B shows piston 370 with diameter matching diameter D2, with piston 370 mounted on rod 355; FIG. 6C shows gasket 380 with external diameter matching diameter D1, whereby gasket 380 is mounted on piston 370. Referring now to FIG. 6D, gasket 380 is shown with optional barb or lip 382 having diameter of Db. Diameter Db is smaller relative to diameter D2, with difference of from about 0.050 mm to about 3 mm, more preferably 0.1 mm to 2 mm, such as 0.5 mm or 1 mm. Barb or lip 382 serves to ensure tight engagement of gasket 380 with piston 370 during advancement through large diameter compartment 322, and then separation of piston 370 from gasket 380 by pushing piston 370 over barb 382 whereby piston 370 disengages from gasket 380 and enters smaller diameter compartment 324. Referring now to FIG. 6E, an embodiment of first syringe 310 corresponding to cross-sectional views of FIGS. 5A-C is shown in a prospective view.

Figure 7A:
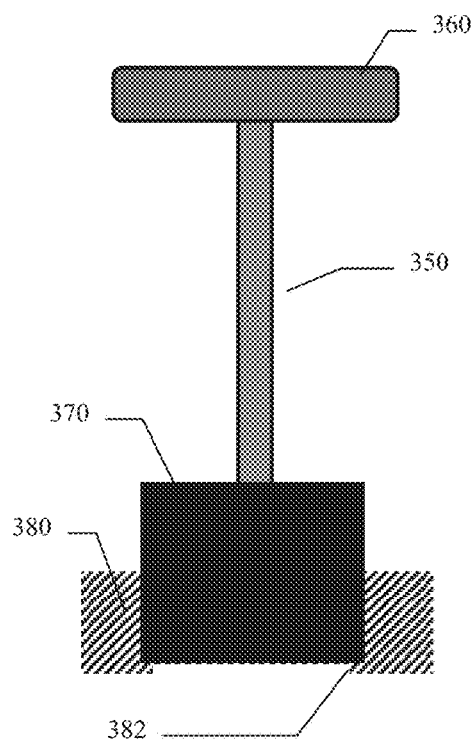
FIGS. 7A-E show embodiments of the present invention.
Figure 7B:
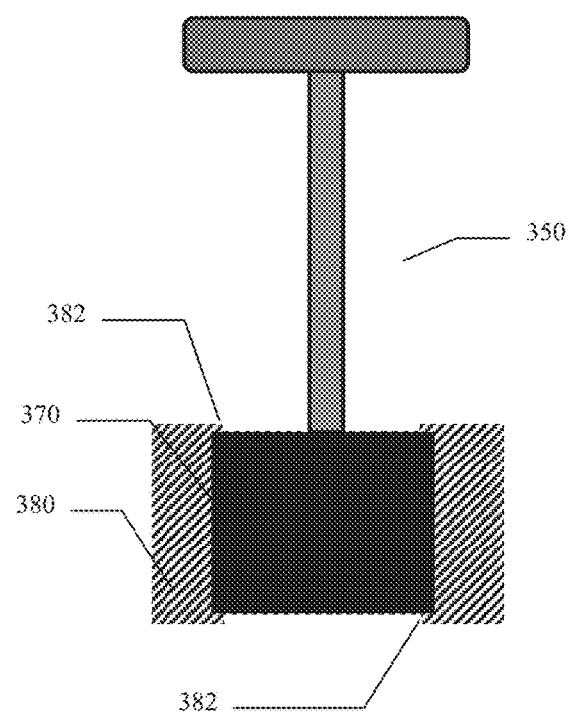
Figure 7C:
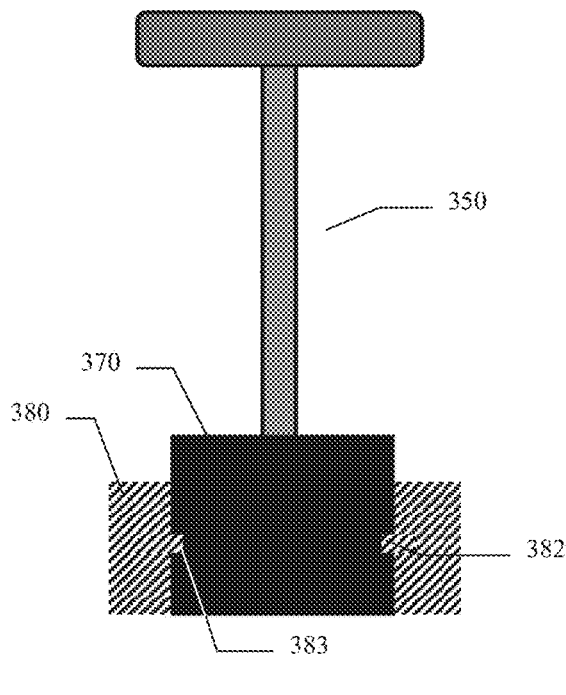
Figure 7D:
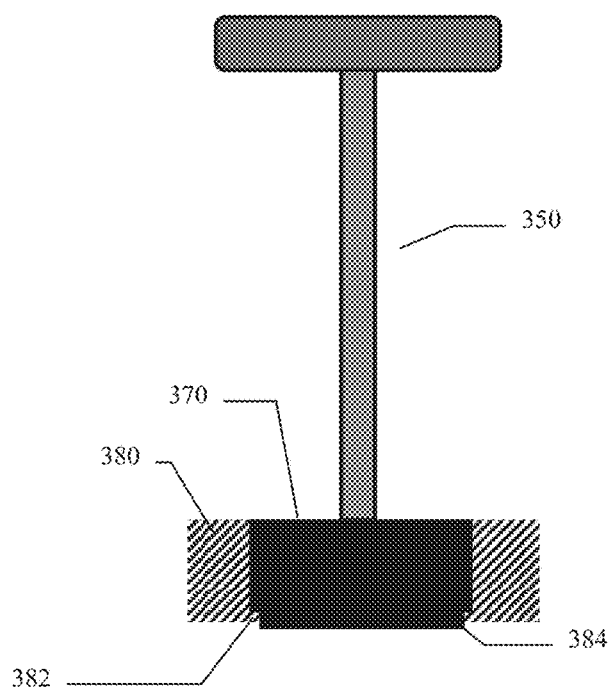
Figure 7E:
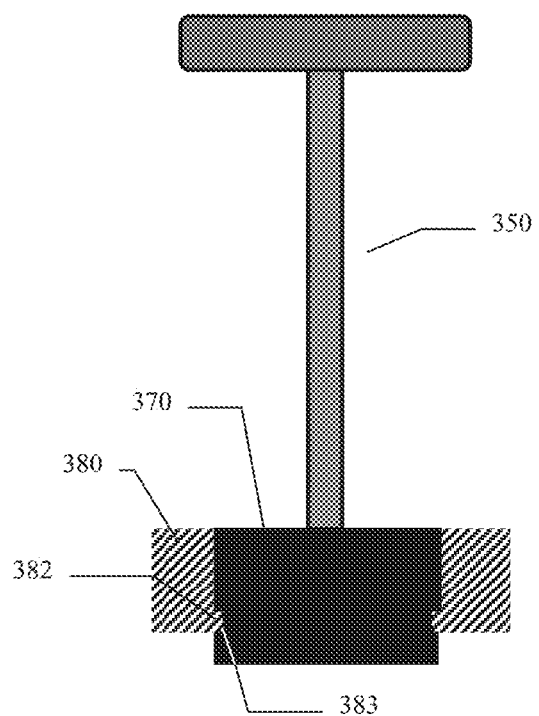

Referring now to FIGS. 7A-E, several embodiments and arrangements of gasket 380 and piston 370 are shown in a schematic cross-sectional view, for position of gasket 380 engaged with piston 370 within large diameter compartment 322. FIG. 7A shows gasket 380 having optional barb 382 on proximal side of gasket 380 adapted to increase force necessary to disengage piston 370 from gasket 380. FIG. 7B shows gasket 380 having optional barb 382 on both proximal and distal side of gasket 380 adapted to increase force necessary to disengage piston 370 from gasket 380. FIG. 7C shows barb 382 positioned inside gasket 380 and fitting within a cutout or grove 383 within piston 370. FIG. 7D shows piston 370 having an area of smaller diameter 384 at proximal end, facilitating entry of piston 370 into small diameter compartment 324 (not shown in FIG. 7 D). FIG. 7E shows barb 382 positioned inside gasket 380 and fitting within a cutout or grove 383 within piston 370 which is extending beyond gasket 380 for more reliable engagement of gasket 380 and piston 370.

Figure 9A:
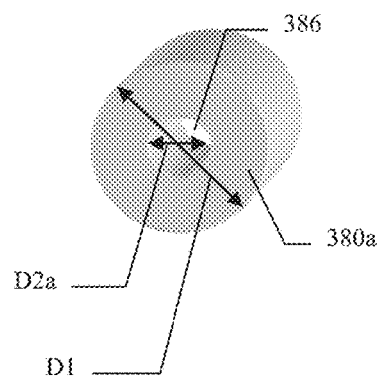
FIGS. 9A-9G show embodiments of the present invention.
Figure 9B:
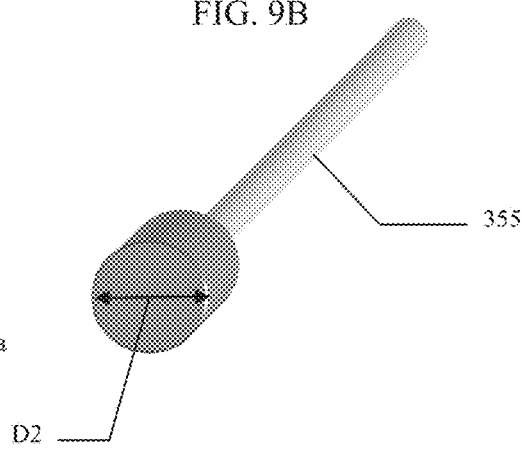
Figure 9C:
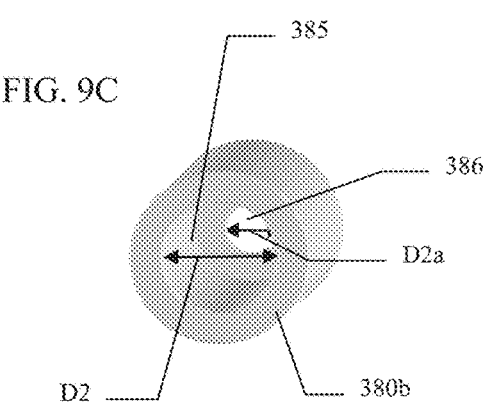
Figure 9D:
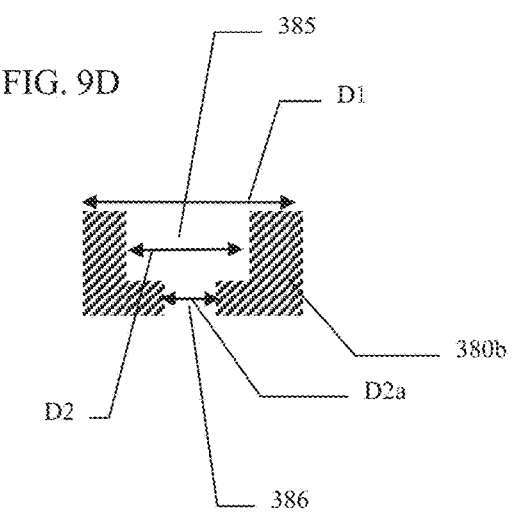
Figure 9E:
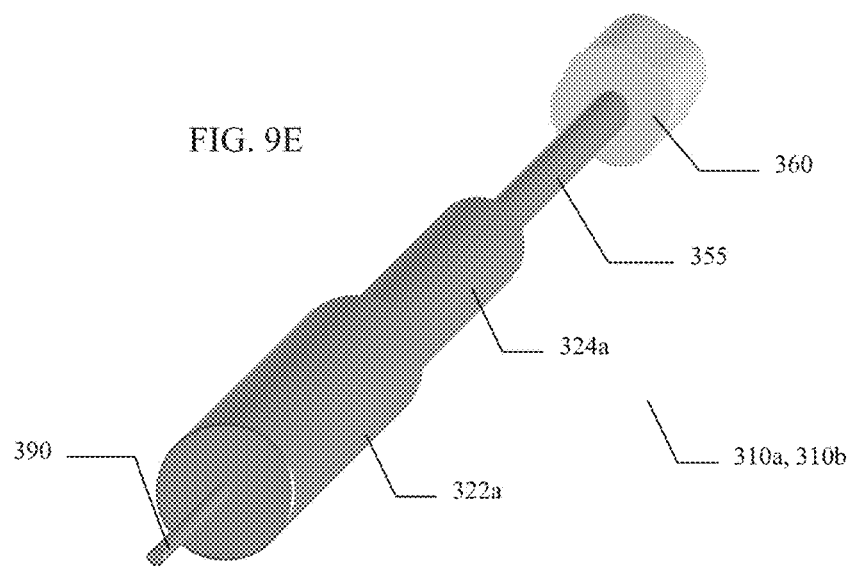

The embodiments of FIGS. 7B, 7C, and 7E also enable the movement of plunger 350 not only towards proximal end 330, but also towards distal end 340, without disengaging piston 370 from gasket 380 in large diameter compartment 322. This enables filling of syringes 310 by pulling plunger 350 from the position shown in FIG. 5C, towards distal end 340, with fluid entering syringe 310 through nozzle 390. During filling of the syringe 310, as piston 370 enters large diameter compartment 322, piston 370 engages with gasket 380 with the help of barb 382 and optionally cutout 383, and then piston 370 continues moving though large diameter compartment 322 towards distal end 340 engaged with gasket 380, resulting in filling of syringe 310 through nozzle 390. Referring now to FIGS. 8A-D, alternative embodiments of first syringe 310a and 310b are presented in a schematic cross-sectional view. Differentiating from the embodiments shown in FIGS. 5A-C, in embodiments of first syringe 310a and 310b shown in FIGS. 8A-D, barrel 320a comprises a first retention compartment or large diameter compartment 322a positioned closer to proximal end 330 and a second retention compartment or small diameter compartment 324a positioned closer to distal end 340. In the embodiments presented in FIGS. 8A-D, gaskets 380a and 380b are positioned in large diameter compartment 322a and have openings 386 with diameter D2a smaller than diameter D2 of piston 370, such as from 10% smaller to 90% smaller. In the embodiment presented in FIGS. 8B and 8D, gasket 380b, while similar to gasket 380a, also has a gasket cutout 385 adapted to snugly accommodate piston 370. The elements of embodiments of FIGS. 8A-C are shown in more details in FIGS. 9A-G. FIG. 9A shows ring-shaped gasket 380a of FIGS. 8A and 8C having external diameter matching D1, and opening 386 having diameter D2a. FIG. 9B shows piston 370 with diameter matching diameter D2, piston 370 mounted on rod 355. FIGS. 9C and 9D show gasket 380b of FIGS. 8B and 8D similar to gasket 380a but further having cutout 385 of diameter D2. FIG. 9E shows embodiment of first syringe 310a or 310b corresponding to cross-sectional views of FIGS. 8A-D but shown in a prospective view.

Figure 9F:
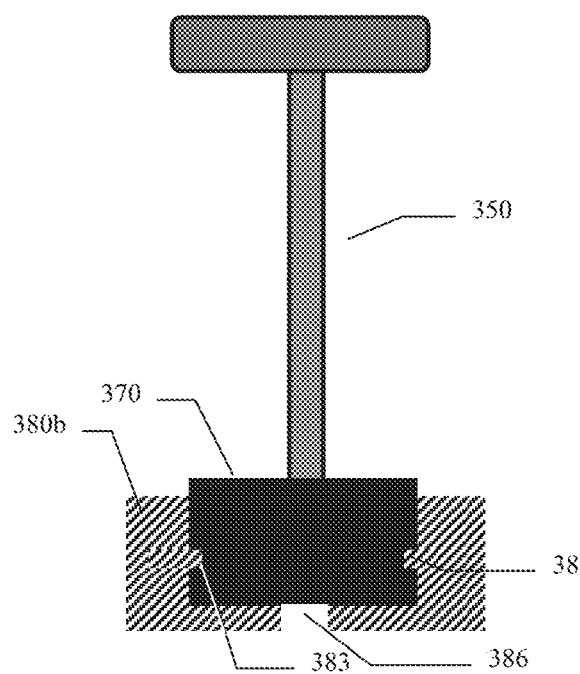
Figure 9G:
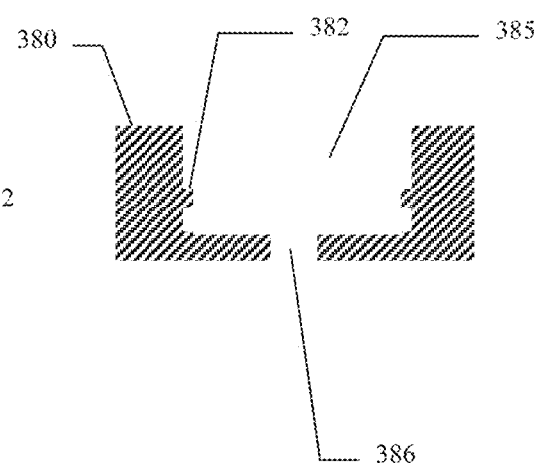

FIGS. 9F and 9G show an embodiment of gasket 380*b* and piston 370, with optional barb 382 positioned inside gasket 380 and fitting within an optional cutout or grove 383 within piston 370 for more reliable engagement of gasket 380*b* and piston 370. FIG. 9F shows gasket 380*b* and piston 370 engaged, while FIG. 9G shows only gasket 380*b*.

FIGS. 8A and 8B show respectively the first syringe 310*a* and 310*b* prior to expressing component A or during expressing component A from small diameter compartment 324*a* by advancing piston 370 towards proximal end 330, but with piston 370 remaining within small diameter compartment 324*a*. Gaskets 380*a* and 380*b* always remain within large diameter compartment 322*a*. In operation, piston 370 advances through small diameter compartment 324*a* towards proximal end 330 or towards nozzle 390 moving component A from small diameter compartment 324*a* through openings 386 and through large diameter compartment 322*a* thus expressing component A through nozzle 390 at a lower volumetric expression rate. As piston 370 approaches large diameter compartment 322*a*, it engages with gasket 380*a* or 380*b*, blocking opening 386, after which piston 370 continues advancing within large diameter compartment 322*a* together with gaskets 380*a* or 380*b*.

Referring now to FIGS. 8C and 8D, first syringes 310*a* and 310*b* are shown in further operation, after expressing component A from small diameter compartment 324*a* and beginning expression from large diameter compartment 322*a*. As can be seen, within large diameter compartment 322*a* piston 370 advances towards proximal end 330 engaged with gaskets 380*a* or 380*b*, with volumetric expression rate from syringes 310*a* and 310*b* increasing, provided that the linear speed of advancing plunger 350 remains the same. Openings 386 are big enough for the fluid, such as component A, to easily pass though openings 386 as piston 370 advances through small diameter compartment 324*a*, without gaskets 380*a*, 380*b* moving within large diameter compartment 322*a*. Openings 386 can be adjusted so that for higher viscosity fluids the cross-sectional size of openings is greater. The combination of the cross-sectional area of opening 386 and the tight fit of gaskets 380*a*, 380*b* within the syringe prevents the movement of the gaskets 380*a*, 380*b* before piston 370 engages with gaskets 380*a*, 380*b* at the border between large diameter compartment 322*a* and small diameter compartment 324*a*, whereby piston 370 starts physically pushing on gaskets 380*a*, 380*b* thus moving gaskets through large diameter compartment 322*a*. Openings 386 can be non-circular or circular, in which case openings 386 can be from about 1 mm in diameter to about 10 mm in diameter, more preferably 2 to 8 mm in diameter, such as 3 mm, 4 mm, or 5 mm in diameter.

Similarly to the embodiments of FIGS. 7B, 7C, 7E, the embodiment of FIGS. 9F and 9G also enables the movement of plunger 350 not only towards proximal end 330, but also towards distal end 340, without disengaging piston 370 from gasket 380*b* in large diameter compartment 322*a*. This enables filling of syringes 310*b* of FIGS. 8B, 8D by pulling plunger 350 from initial position where piston 370, engaged with gasket 380*b* in proximity to proximal end 330, towards distal end 340, with fluid entering syringe 310*b* through nozzle 390. During filling of the syringe 310*b*, piston 370 moves through large diameter compartment 322*a* engaged with gasket 380*b* with the help of barb 382 and cutout or groove 383, as shown in FIG. 8D (barb 382 and cutout or groove 383 are not shown in FIG. 8D). As piston 370 enters small diameter compartment 324*a*, piston 370 disengages from gasket 380*b*, and then piston 370 continues moving though small diameter compartment 324*a* towards distal end 340, resulting in filling of syringe 310 through nozzle 390 as also shown in FIG. 8B (barb 382 and cutout or groove 383 are not shown in FIG. 8B).

Figure 10A:
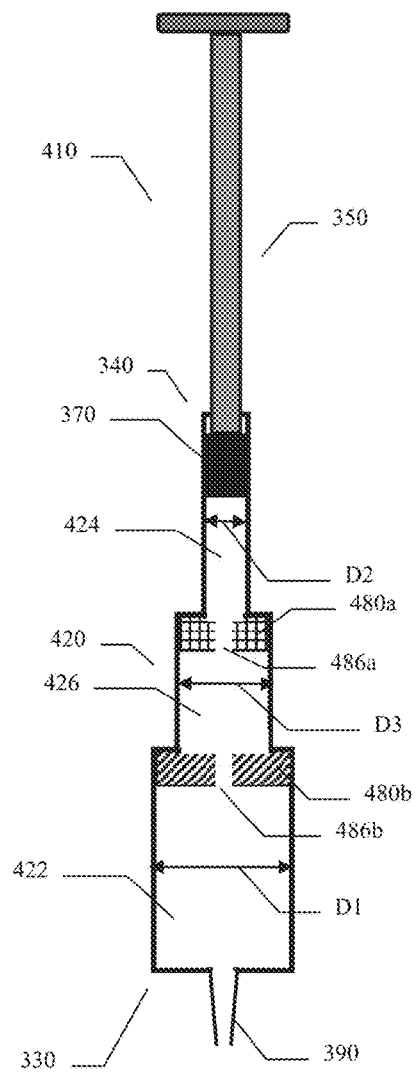
FIGS. 10A-C show embodiments of the present invention.
Figure 10B:
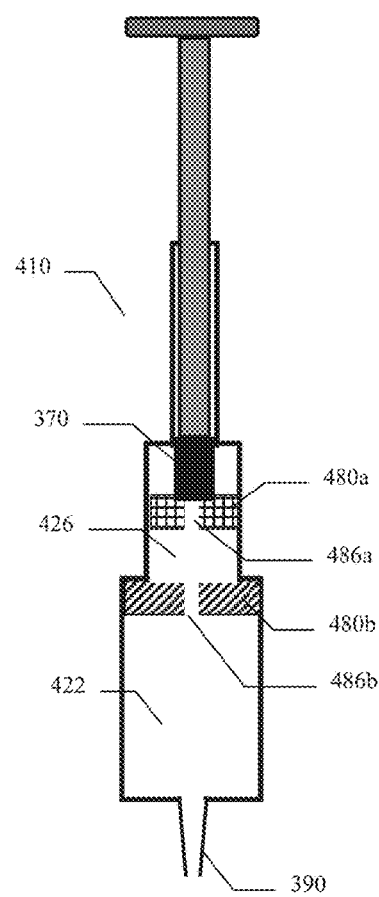
Figure 10C:
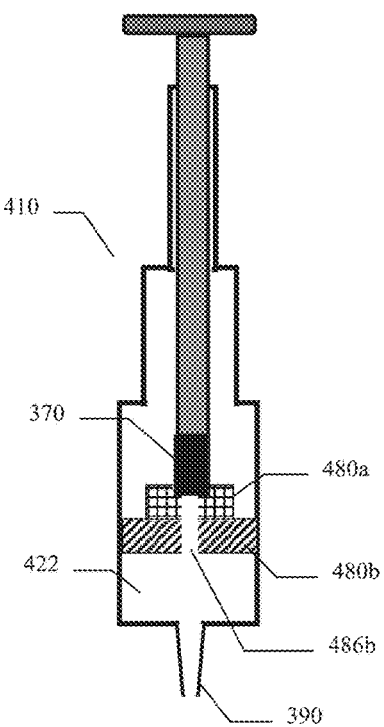

Embodiments of first syringe 310, 310*a*, and 310*b* illustrated above provide for one step-wise change in expression rate of component A. According to another embodiment of the present invention, more step-wise changes in expression rate can be accomplished by having more than two compartments of different diameters comprising generally tubular hollow barrel of first syringe, such as three compartments of different diameters, with two step-wise changes in expression rate. As shown in FIGS. 10A-C, in another embodiment of the present invention, first syringe 410 comprises generally tubular hollow barrel 420 having a proximal end 330 and an opposing distal end 340 spaced axially behind proximal end 330. Barrel 420 comprises a first retention compartment or large diameter compartment 422 having internal diameter D1 and positioned closer to proximal end 330, a second retention compartment or small diameter compartment 424 having internal diameter D2 and positioned closer to distal end 340, and an intermediate diameter compartment 426 having internal diameter D3 and positioned between large diameter compartment 422 and small diameter compartment 424. Nozzle 390, which is located on proximal end 330 of barrel 420, expresses component A from first syringe 410. An elongated plunger 350 projects axially rearward out of distal end 340 and axially slidable in barrel 420 driving piston 370 from distal end 340 to proximal end 330. Piston 370 has a diameter closely matching diameter D2, for tight but slidable fit inside small diameter compartment 424.

Ring-shaped gasket 480*a* in intermediate diameter compartment 426 has outside diameter that closely matches diameter D3 for tight but slidable fit inside intermediate diameter compartment 426. Ring-shaped gasket 480*b* in large diameter compartment 422 has outside diameter that closely matches diameter D1 for tight but slidable fit inside large diameter compartment 422. Gaskets 480*a* and 480*b* have openings 486*a* and 486*b* with diameter smaller than diameter D2 of piston 370, such as from 10% smaller to 90% smaller.

FIG. 10A shows the first syringe 410 prior to expressing component A or during expressing component A from small diameter compartment 424 by advancing piston 370 towards proximal end 330, but with piston 370 remaining within small diameter compartment 424. Gasket 480*a* remains within intermediate diameter compartment 426 and large diameter compartment 422. Gasket 480*b* remains within large diameter compartment 422. In operation, piston 370 advances through small diameter compartment 424 towards proximal end 330 moving component A from small diameter compartment 424 through openings 486*a* and 486*b* and through intermediate diameter compartment 426 and large diameter compartment 422 thus expressing component A through nozzle 390 at a low volumetric expression rate. As piston 370 approaches intermediate diameter compartment 426, it engages gasket 480*a*, blocking opening 486*a*. As shown in FIG. 10B, piston 370 then continues advancing within intermediate diameter compartment 426 with gasket 480*a* moving in front of piston 370. As piston 370 with gasket 480*a* approaches large diameter compartment 422, gasket 480*b* engages, blocking gasket opening 486*b*. As shown in FIG. 10C, piston 370 then continues advancing within large diameter compartment 422 with gaskets 480*a* and 480*b* moving in front of piston 370.

As it is clear from the above description and FIGS. 10A-C, the volumetric expression rate is lowest when piston 370 advances within small diameter compartment 424; volumetric expression rate is intermediate when piston 370 advances within intermediate diameter compartment 426; and volumetric expression rate is highest when piston 370 advances within large diameter compartment 422; the changes in volumetric expression rate occur step-wise, increasing as piston moves form one compartment to another, provided that the linear speed of advancing plunger 350 remains essentially the same.

In certain embodiments of the present invention, first syringe can have a plurality of compartments of increasing size, resulting in multiple step-wise increases in expression rate, each increase can be relatively small, such as increase of 10% to 50%, such as 20% increase. Referring now to FIG. 11, first syringe 510 has barrel 520 comprising 5 compartments, with piston 370 disposed in smallest compartment, and gaskets 580a, 580b, 580c, and 580d positioned in compartments of increasing diameter. Operation of first syringe 510 is similar to described above for first syringe 410.

As shown above, in certain embodiments of the present invention, first syringe can have a plurality of compartments arranged sequentially from distal end to proximal end, whereby diameter of the compartments goes from smaller to larger from distal end to proximal end, or vice versa, from larger to smaller from distal end to proximal end, resulting in respectively increase in expression rate, or decrease in expression rate. In other embodiments described below, diameter of the compartments goes from smaller to larger and then back to smaller from distal end to proximal end, or vice versa from larger to smaller and then back to larger from distal end to proximal end, resulting in respectively lower-higher-lower expression rate, or higher-lower-higher expression rate.

Figure 12A:
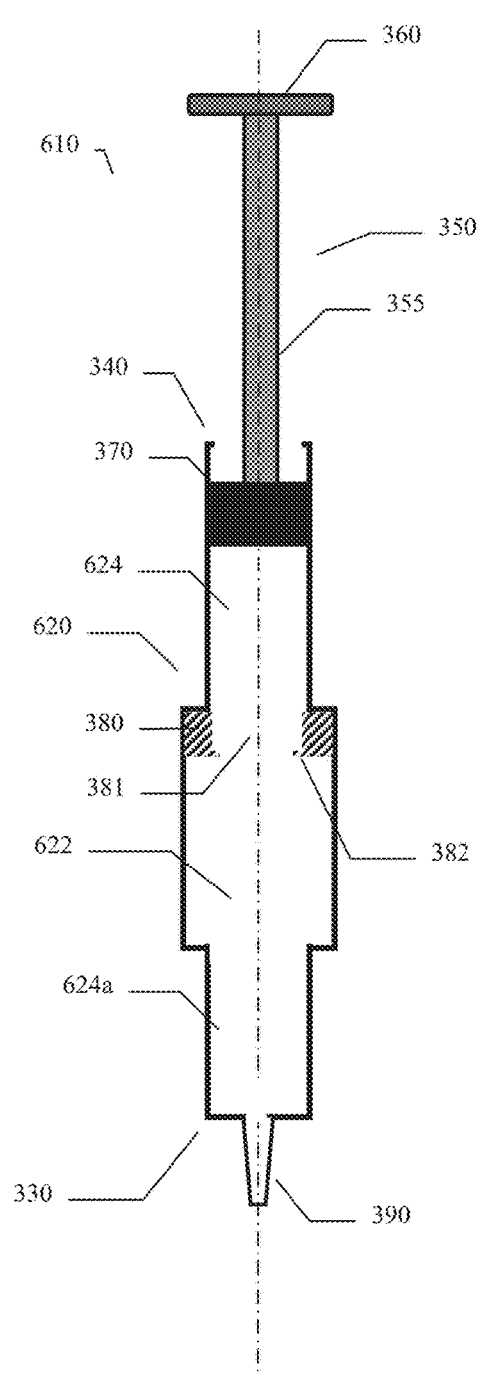
FIGS. 12A-B show embodiments of the present invention.

Referring now to FIG. 12A, in one embodiment of the present invention, first syringe 610 comprises barrel 620 which comprises a plurality of compartments arranged sequentially from distal end 340 to proximal end 330, whereby diameter of compartments goes from smaller to larger and then back to smaller, resulting in expression rate that is initially lower, then increases, and then goes back to lower rate. Barrel 620 comprises at the distal end 340 second retention compartment or small diameter compartment 624, and at the proximal end 330 another second retention compartment or small diameter compartment 624a, with first retention compartment or large diameter compartment 622 disposed between small diameter compartments 624a and 624. Small diameter compartments 624a and 624 have the same internal diameters equal to external diameter of piston 370 and same or different lengths, with internal diameters of small diameter compartments 624a and 624 in all cases smaller than the internal diameter of large diameter compartment 622. Piston 370 in small diameter compartment 624 and ring-shaped gasket 380 having opening 381 and barb or lip 382 are disposed in large diameter compartment 622.

In operation, piston 370 advances through small diameter compartment 624, resulting in low expression rate; then approaching large diameter compartment 622 piston 370 engages with gasket 380, after which piston 370 engaged with gasket 380 advances through large diameter compartment 622, resulting in high expression rate; approaching small diameter compartment 624a piston 370 disengages from gasket 380 and then piston 370 advances through small diameter compartment 624a, resulting in low expression rate.

Figure 12B:
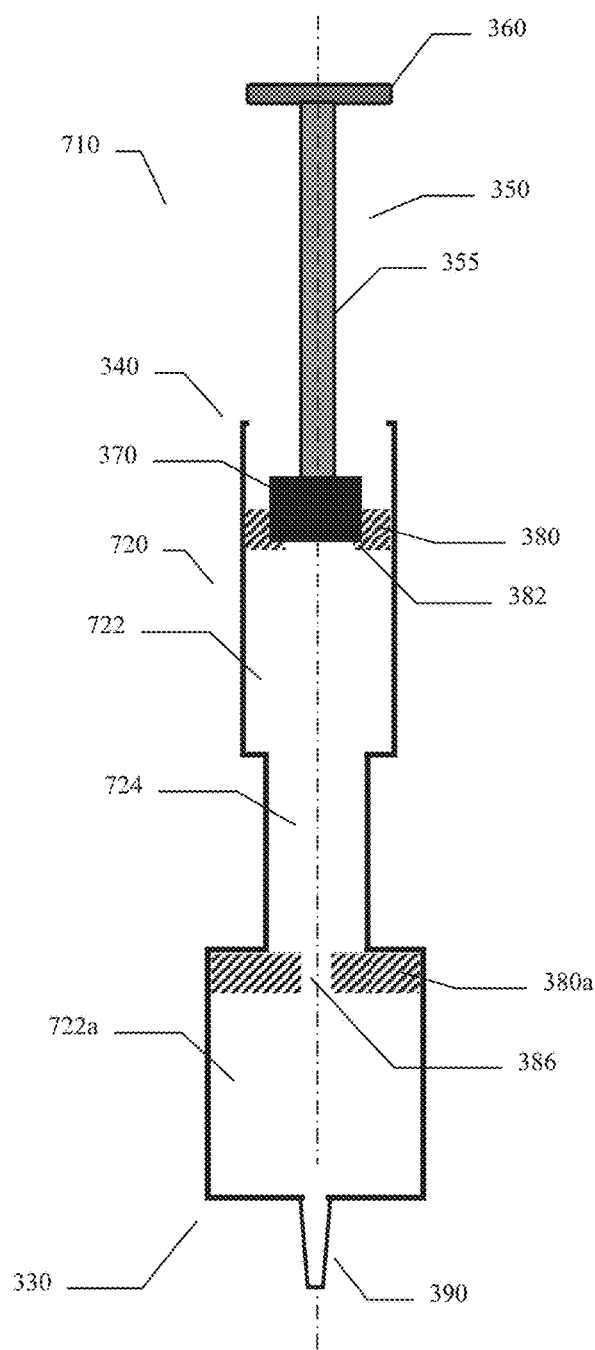

Referring now to FIG. 12B, in another embodiment of the present invention, first syringe 710 comprises barrel 720 which comprises a plurality of compartments arranged sequentially from distal end 340 to proximal end 330, whereby diameter of compartments goes from larger to smaller and then back to larger, resulting in expression rate that is initially higher, then decreases, and then goes back to higher rate. Barrel 720 comprises first retention compartment or large diameter compartment 722 at the distal end 340, and another first retention compartment or large diameter compartment 722a at the proximal end 330, with second retention compartment or small diameter compartment 724 having internal diameter equal to diameter of piston 370, with the small diameter compartment 724 disposed between larger diameter compartments 722a and 722. Larger diameter compartments 722a and 722 can have the same diameters and lengths or different diameters and lengths (as shown in FIG. 12B), but internal diameters of larger diameter compartments 722a and 722 are in all cases larger than the internal diameter of small diameter compartment 724. Piston 370 positioned in large diameter compartment 722 engages with ring-shaped gasket 380 having barb or lip 382. Ring-shaped gasket 380a with opening 386 is positioned in large diameter compartment 722a.

In operation, piston 370 together with ring-shaped gasket 380 advances through large diameter compartment 722, resulting in high expression rate; before entering small diameter compartment 724 piston 370 disengages from gasket 380, with gasket 380 remaining in large diameter compartment 722, after which piston 370 advances through small diameter compartment 724, resulting in low expression rate; upon entering large diameter compartment 722a, piston 370 engages gasket 380a and blocks opening 386, after which piston 370 advances together with gasket 380a through large diameter compartment 722a, resulting in high expression rate.

Figure 13A:
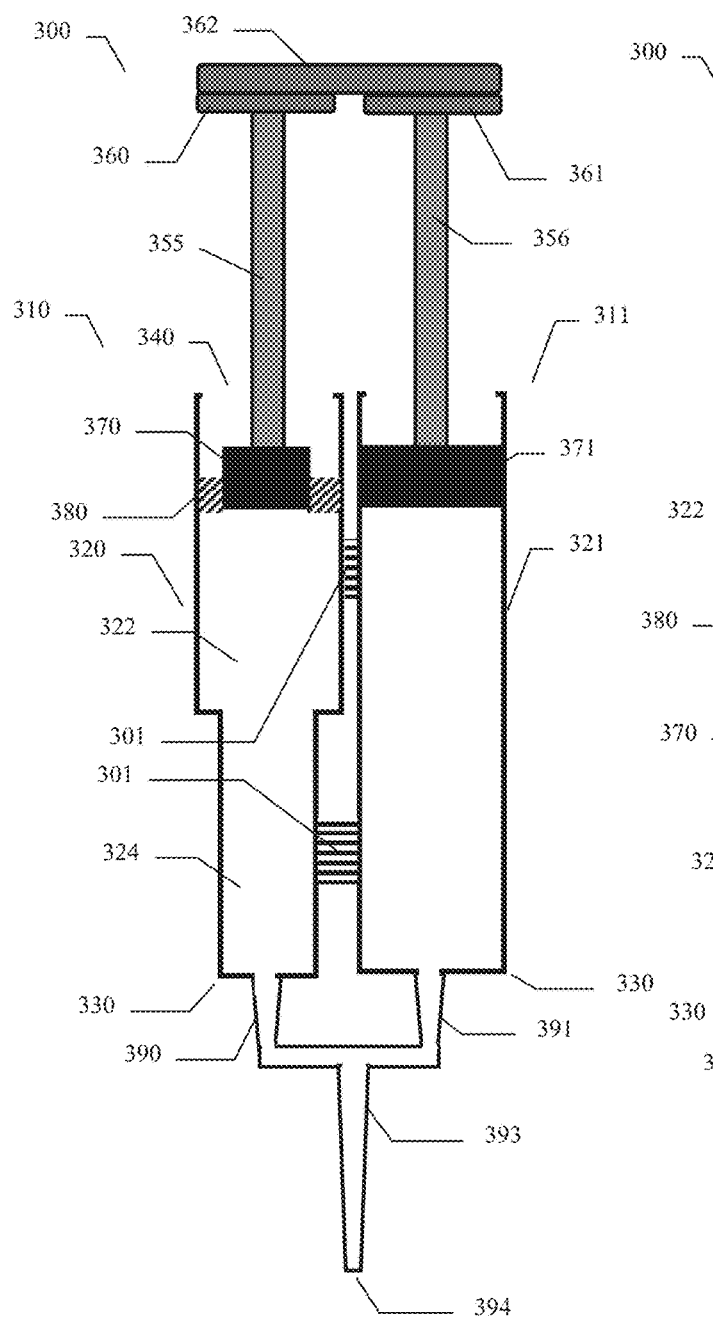
FIG. 13A-B show embodiments of the present invention.
Figure 13B:
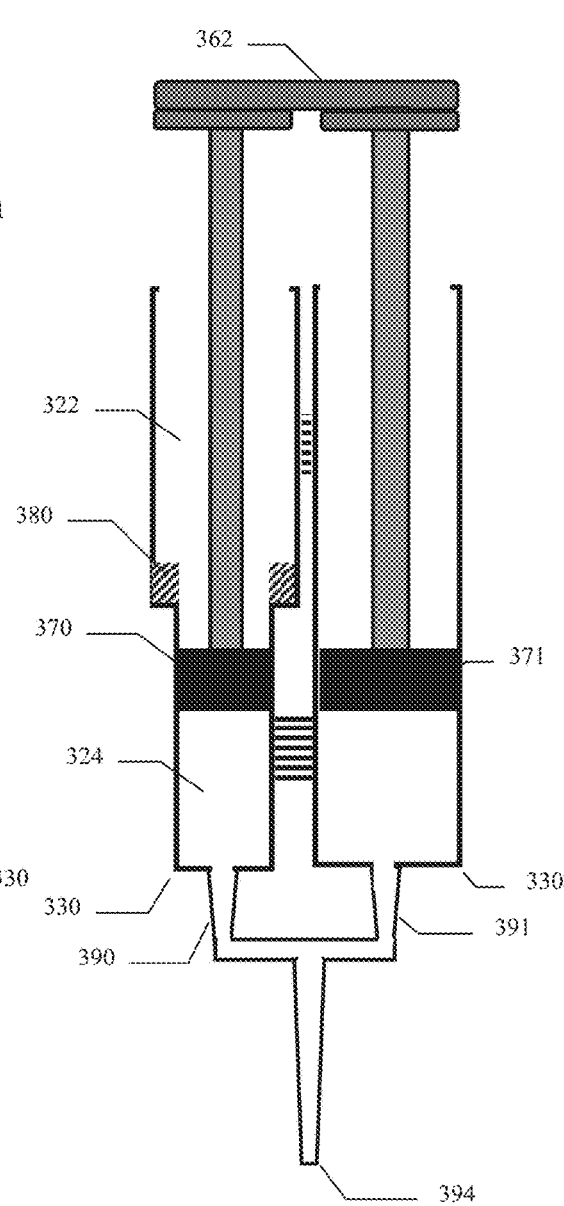
Figure 14:
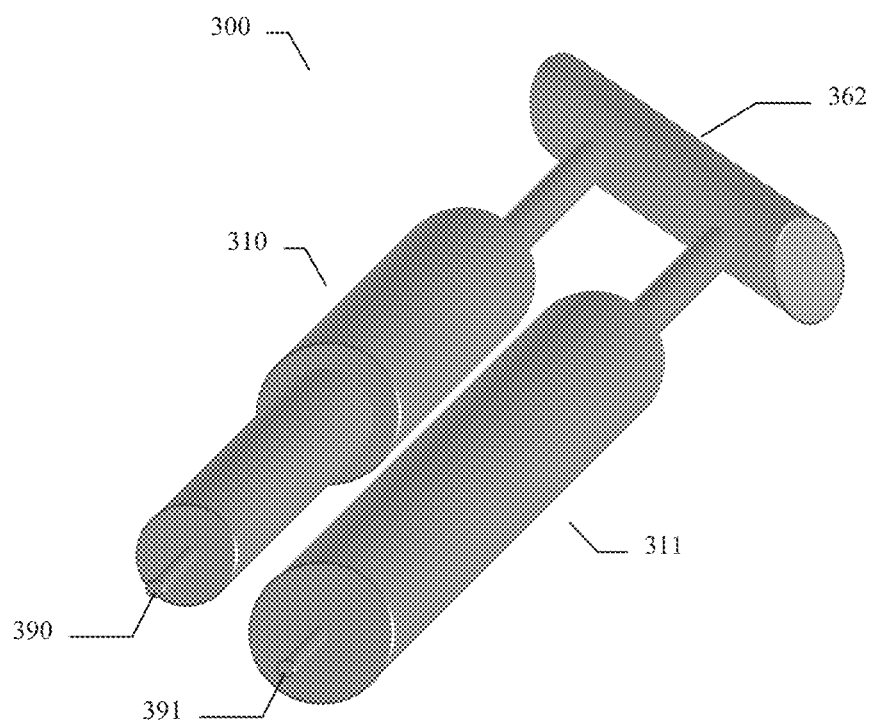
FIG. 14 shows embodiment of the present invention.
Figure 16:
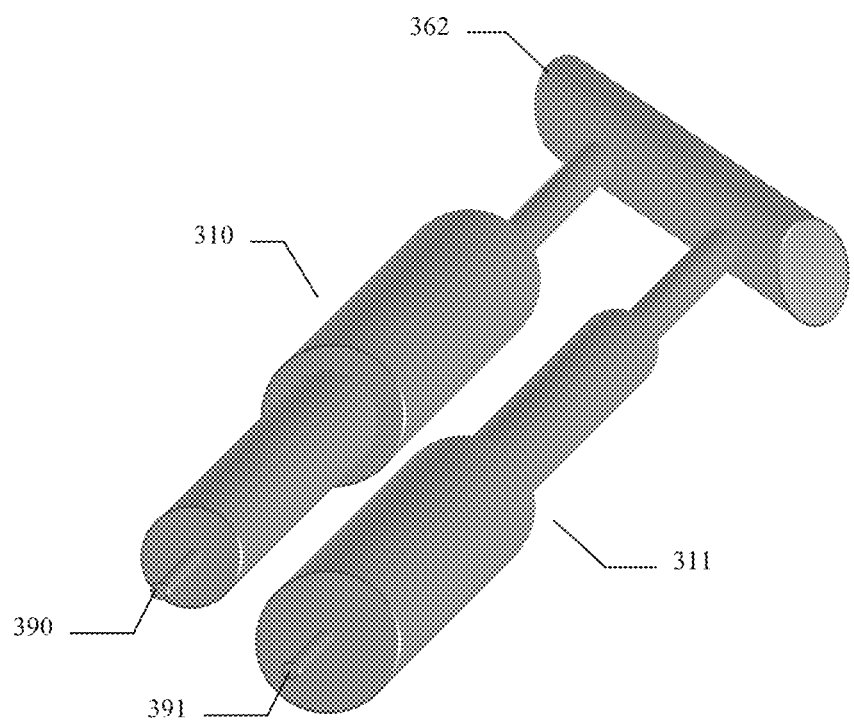
FIG. 16 shows embodiment of the present invention.

Referring now to FIGS. 13A-B and 14, dual syringe delivery device 300 of the present invention is shown in a schematic cross-sectional view and in a schematic 3D view, with device 300 comprising first syringe 310 having barrel 320 containing component A and second syringe 311 having barrel 321 containing component B, with barrel 320 and 321 optionally joined side-by-side by connecting means or linkages 301 in a fixed position relative to each other (linkages 301 not shown in FIG. 14). In the embodiment shown in FIG. 13, first syringe 310 is substantially similar to embodiment of first syringe 310 as shown in FIGS. 5A-C. Second syringe 311 can be a standard construction syringe with a hollow cylindrical barrel 321 of the same diameter throughout, which will provide a constant relative expression rate. Piston 371 of second syringe 311 is mounted on rod 356 on proximal end, with optional handle 361 mounted on rod 356 on distal end. Optional handles 360 and 361 are interconnected with a bar 362 to ensure joint movement of pistons 370 and 371 for simultaneous expression of components A and B. Optionally, handles 360 and 361 are not used and instead bar 362 is directly attached to rods 355 and 356, as shown in FIG. 14. Nozzles 390 and 391 are optionally connected to an optional mixing manifold 393 for intermixing and simultaneous expression of the resulting mixture through a single expression port 394. In an alternative embodiment (as shown in FIG. 14) no mixing manifold 393 is used, and components A and B are simultaneously expressed through nozzles 390 and 391 without mixing.

In operation, as the user depresses bar 362, components A and B are expressed at an relative expression ratio proportional to square of the ratio of diameters of compartments of first syringe 310 and second syringe 311 where pistons 370 and 371 are positioned. Pistons 370 and 371 are advancing at the same speed towards proximal end 330, with the distance from pistons 370 and 371 to proximal end 330 can be substantially the same throughout the expression of components A and B. In the embodiment shown in FIGS. 13A-B and 14, the initial relative expression ratio of components A and B is about 1:1 and corresponds to positions of pistons 370 and 371 shown in FIG. 13A, with piston 370 in large diameter compartment 322. As expression of components A and B progresses, piston 370 reaches small diameter compartment 324 of barrel 320 of first syringe 310 and disengages from gasket 380, whereby relative expression rate of component A decreases, corresponding to positions of pistons 370 and 371 shown in FIG. 13B. The relative expression rate of component B remains the same throughout. For the geometry shown in the FIG. 13, expression ratio will change from (component A:component B) equal to about 1:1 to expression ratio equal to about 0.4:1.

The speed of depressing of bar 362 by a user can affect the overall expression rate of both components A and B. However the volumetric expression ratio is independent of the speed of advancing pistons and gaskets in first syringe 310 and second syringe 311, with ratio of component A:component B expression remaining independent of the speed of coating delivery defined by the speed of depressing the bar 362. Thus for the embodiment in FIGS. 13A-B and 14, the expression ratio will change from (component A:component B) equal to about 1:1 to expression ratio equal to about 0.4:1 while the coating delivery speed or spray rate from single expression port 394 can vary over a wide range of speeds, with coating delivered for instance at 0.1 ml/s, 0.5 ml/s, 1 ml/s, or 5 ml/s.

Optionally, there can be a pause when switching from the components mixed in the initial expression ratio of components A and B to the second (or final) expression ratio, such as from equal to about 1:1 to expression ratio equal to about 0.4:1 as in the description above. The optional pause can be from about 1 second to a few minutes, such as 5 seconds, 10 seconds, 30 seconds, or 60 seconds. The optional pause can be used to allow partial or full curing of the applied coating corresponding to the mixture of components in the initial expression ratio, prior to applying the mixture of components in the second (or final) expression ratio.

In other embodiments of device 300 of present invention, first syringe 310 can be any of previously described embodiments of first syringe, including first syringe 310, 310a, 310b, 410, 510, 610, 710, and variants thereof as described above. Second syringe 311 can be any standard construction syringe with a hollow cylindrical barrel 321 of the same diameter throughout, which will provide constant expression rate. In alternative embodiments of the present invention, second syringe 311 can also be of construction corresponding to or similar to embodiments of first syringe described above, including first syringe 310, 310a, 310b, 410, 510, 610, 710, and variants thereof as described above. One embodiment of device 300 having both first syringe 310 and second syringe 311 having variable relative expression rate is shown in FIGS. 15A-C and 16.

Referring now to FIGS. 15A-C and 16, embodiment of dual syringe delivery device 300 of the present invention is shown in a schematic cross-sectional view and in a schematic 3D view, with device 300 comprising two syringes, similarly to the design shown in FIGS. 13A-B and 14, with first syringe 310 containing component A and second syringe 311 containing component B. In this embodiment, first syringe 310 is substantially equivalent to embodiment of first syringe 310 as shown in FIGS. 5A-C and second syringe 311 is substantially equivalent to embodiment of first syringe 310b as shown in FIGS. 8B and 8D. First syringe 310 has a first retention compartment or large diameter compartment 322 positioned closer to distal end 340 and a second retention compartment or small diameter compartment 324 positioned closer to proximal end 330, resulting in expression of component A changing from higher relative expression ratio to lower relative expression ratio. Second syringe 311 has a first retention compartment or large diameter compartment 322a positioned closer to proximal end 330 and a second retention compartment or small diameter compartment 324a positioned closer to distal end 340, resulting in expression of component B changing from lower relative expression ratio to higher relative expression ratio.

In operation, as the user depresses bar 362, components A and B are expressed at a relative expression ratio proportional to square of the ratio of diameters of compartments of first syringe 310 and second syringe 311 where pistons 370 and 371 are positioned. In the embodiment shown in FIG. 15, the initial components expression ratio A:B is about 2.25:1 and corresponds to positions of pistons 370 and 371 shown in FIG. 15A in compartments 322 and 324a respectively. As expression of components A and B progresses, and piston 371 reaches large diameter compartment 322a of second syringe 311, piston 371 engages gasket 380b, whereby expression rate of component B increases, corresponding to positions of pistons 370 and 371 shown in FIG. 15B. At the same time expression rate of component A remains the same. For the geometry shown in the FIG. 15B, components expression ratio A:B will be about 2.25:2.25 or 1:1 at this stage in the delivery of the mixture of components A and B. As expression of components A and B progresses further, piston 370 reaches small diameter compartment 324 of first syringe 310, whereby piston 370 disengages from gasket 380, and continues advancing through smaller diameter compartment 324 of first syringe 310, whereby expression rate of component A decreases, corresponding to positions of pistons 370 and 371 shown in FIG. 15C. At the same time expression rate of component B remains the same. For the geometry shown in the FIG. 15C, components expression ratio A:B will be about 0.45:1 at this stage in the delivery of the mixture of components A and B. Thus the mixing ratio changed from 2.25:1 to 1:1 to 0.45:1, with overall change in mixing ratio is about 5 times from start of expression to end of expression, with two step-wise changes. In an alternative embodiment, device 300 provides for one step-wise change in the mixing ratio, with length of small diameter compartment 324 of first syringe 310 equal to length of large diameter compartment 322a of second syringe 311. In this embodiment, only one step-wise change in relative expression or mixing ratio will be provided, with the change in relative expression ratio from about 2.25:1 to about 0.45:1.

Inside diameters of compartments of syringes are typically from about 5 mm to about 40 mm, more preferably from about 8 mm to about 25 mm, such as 10 mm, 15 mm, and 20 mm. Alternative embodiments of the syringes of the instant invention also include non-circular cross-sections, such as elliptical cross-sections, polygonal, etc. Outside diameters of pistons and of ring-shaped gaskets are described as matching diameters to inside diameters of compartments for tight slidable fit. Matching indicates that diameters are substantially equal, or slightly larger or smaller, by 1-500 microns, more preferably 5-200 microns, such as 50 or 100 microns larger or smaller than corresponding diameter of barrel compartment where piston or gasket are slidably moving to ensure leak-free expression of components. Similarly, gasket cutout 385 is adapted to snugly accommodate piston 370, with inside diameter of gasket cutout matching outside diameter of piston, such as substantially equal to plus or minus 1 to 300 microns, more preferably 5 to 50 microns. Lengths of compartments are from about 1 cm to about 40 cm, more preferably 5 cm to 20 cm, such as 10 cm. Materials for making components of syringes, such as barrels, pistons, etc., are known to these skilled in the art and may be selected from polymers, glass, metals, rubber, silicone, and other known materials. Methods of manufacturing of the syringes are known to these skilled in the art, and include, but not limited to, molding, machining, and assembly from components.

Advantageously, delivery device 300 switches automatically from one mixing ratio to another, thus relieving the surgeon of the necessity to estimate timing and perform a manual switch. Further, advantageously, the coating has two or three or more distinct compositions corresponding to fixed mixing ratios, as opposed to gradually changing compositions, thus properties of each layer of the resulting coating are well characterized and well defined. Advantageously, delivery device 300 delivers set mixing ratios of components independently of the speed of advancement of the plungers. For a constant speed of advancement of the plungers, or for a variable speed of advancement of the plungers, mixing ratios are only dependent upon the position of pistons within barrels, or on how far the expression has progressed.

The timing of the change in mixing ratios of components depends on the rate of expression or rate of advancing the plungers and on the relative lengths of lager diameter and small diameter compartments. According to one embodiment of the present invention, the rate of advancing the plungers is substantially constant, and the step-wise change in mixing rations occurs at about half-time in the sealant expression process, corresponding to identical lengths of large diameter compartment and small diameter compartment. According to another embodiment of the present invention, the user changes the rate of advancing the plungers with a faster advancing at the beginning of the delivery phase and a slower advancement at the end of the delivery phase, which results in an earlier time of switching in mixing rations. According to yet another embodiment of the present invention, the rate of advancing the plungers remains constant, but the lengths of large diameter compartment and small diameter compartment are substantially different, such as the compartment closer to distal end is 10% to 90% shorter, such as 50% shorter. In this embodiment, first mixing ratio is delivered for a shorter time, with second mixing ratio delivered for a longer period of time, resulting in a thinner first layer and thicker second layer on top, forming the two-layer coating of the present invention. In an alternative embodiment, wherein the compartment closer to distal end is 10% to 90% longer, first mixing ratio is delivered for longer time, with second mixing ratio delivered for a shorter period of time, resulting in a thicker first layer and thinner second layer on top of first layer, forming the multi-layer coating of the present invention.

In another embodiment of device of present invention, delivery device comprises at least three syringes, fixedly arranged side by side and joined by optional linkers whereby each of these three syringes can be any of previously described embodiments of syringe having at least one large diameter compartment and at least one small diameter compartment, such as syringes 310, 310a, 310b, 410, 510, 610, 710, and variants thereof as described above, as well as any standard construction syringe with a hollow cylindrical barrel of the same diameter throughout, which will provide a constant expression rate. According to one embodiment, two of the syringes are standard construction syringes with a hollow cylindrical barrel of the same diameter throughout, which will provide a constant expression rate, and one syringe is having at least one large diameter compartment and at least one small diameter compartment, such as syringes 310, 310a, 310b, 410, 510, 610, 710, and variants thereof as described above, providing at least one change in the expression rate during delivery. In an alternative embodiment, one of the syringes is standard construction syringe with a hollow cylindrical barrel of the same diameter throughout, which will provide a constant expression rate, and two syringes have at least one large diameter compartment and at least one small diameter compartment, such as syringes 310, 310a, 310b, 410, 510, 610, 710, and variants thereof as described above, providing at least one change in the expression rate during delivery. In yet another embodiment, all three of the syringes have at least one large diameter compartment and at least one small diameter compartment, such as syringes 310, 310a, 310b, 410, 510, 610, 710, and variants thereof as described above, each of the three syringes providing at least one change in the expression rate during delivery.

According to one embodiment, a distinct resistance change or click can be felt or heard respectively, by a health practitioner when a change is made from one compositional variant or ratio to another, indicating transition to a different coating property. This change in resistance or distinct click may be enabled as a result of engaging or disengaging gasket 380 with or from piston 370 and provides feedback to the health practitioner.

According to another embodiment, the dual or triple syringe delivery device of the present invention comprising two or more syringes which can be connected or disconnected as needed, with one of the syringes in the assembly replaced with another containing a different component, different concentration of the component, or a diluent. The connection can be established with barrels of the syringes optionally joined side-by-side by connecting means or linkages and optionally handles interconnected with a bar to ensure joint movement of pistons, with linkages and bar connecting via lock-in place mechanism as known to these skilled in the art, which can be connected and disconnected as needed, via lock and key or groove and tongue engagement or similar.

Figure 18:
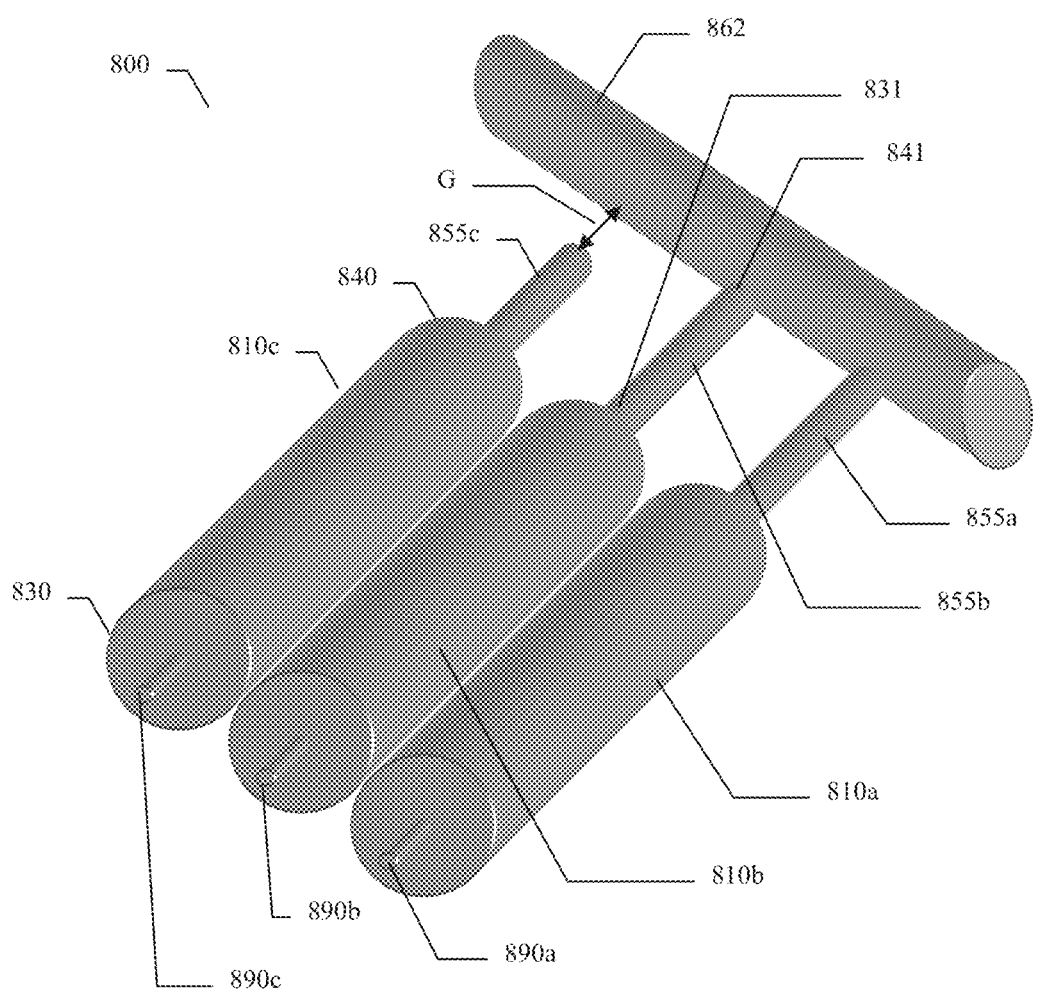
FIG. 18 shows embodiment of the present invention.

Referring now to FIGS. 17A-B and 18, an alternative embodiment of the present invention is presented. Delivery device 800 comprises at least three standard construction cylindrical syringes 810a, 810b, 810c, fixedly arranged side by side and joined by optional linkers 801 (not shown in FIG. 18). Syringes all have pistons 870a, 870b, and 870c sized for slidable fit inside syringes. Rods 855a, 855b, 855c having substantially same length, have front end 831 and rear end 841, with the pistons mounted on at the front end 831. Rods 855a and 855b are connected to a bar 862 at the rear end 841, for simultaneous advancement of pistons 870a, 870b in syringes 810a, 810b. Rod 855c can have an optional handle at the rear end 841 (handle not shown in FIGS. 17-18). Rod 855c is not connected to bar 862, with a gap G between rod 855c and bar 862. Bar 862 projects over rod 855c, whereby bar 862 is positioned above rod 855c so that as bar 862 advances towards proximal end 830, it will touch and engage rod 855c and will push rod 855c from distal end 840 towards proximal end 830. Syringes all have nozzles 890a, 890b, 890c positioned at the proximal end 830 for expressing the contents of the syringe, with nozzles optionally connected to optional manifold 893 terminating in an optional expression port 894 (manifold 893 and expression port 894 are not shown in FIG. 18). Diameters of syringes 810a, 810b, 810c can be the same, as shown in FIG. 17, or different.

In preparation to expression of components from device 800, compartment C1 of syringe 810a is filled with component A, compartment C2 of syringe 810b is filled with component B, and compartment C3 of syringe 810c is filled with component A, component C, or diluent, or another component, such as anti-microbial compound, or combinations thereof. As shown in FIG. 17A, prior to expression from device 800, pistons 870a and 870b are positioned farthest away from front end 830, with the compartments C1 and C2 under pistons 870a and 870b filled with components A and B respectively. Piston 870c is positioned in an intermediate position between proximal end 830 and distal end 840 anywhere from mid-way towards proximal end 830, with compartment C3 under piston 870c filled in one embodiment with component A (with component C, or diluent, or another component, such as anti-microbial compound, or combinations thereof as alternative fluids to fill compartment C3). Gap G or distance from bar 862 to rod 855c is substantially equivalent to distance L2 from pistons 870a and 870b to piston 870c, as shown in FIG. 17A. As can be appreciated from FIG. 17A, upon bar 862 depression by a user, pistons 870a and 870b advance through compartments C1 and C2 towards front end 830 expressing components A and B in the first mixing ratio. As seen in FIG. 17B, as bar 862 approaches rod 855c across the gap G, once pistons 870a and 870b are equidistant with piston 870c from proximal end 830, bar 862 engages rod 855c, whereby pistons 870a, 870b, 870c begin advancing simultaneously through compartments C1, C2, C3 towards proximal end 830. The mixing ratio then automatically changes as material in syringe 810c is added to mixture of materials from syringes 810a and 810b. If all syringes have the same diameters, as shown in FIGS. 17A-B and 18, initial mixing ratio component A:component B will be 1:1, then step-wise changing to 2:1.

In an alternative embodiment (not shown), when internal diameter of syringe 810c is one half of the internal diameters of syringes 810a, 810b, and when syringe 810c is filled with a third component, such as an antimicrobial compound and diluent M, the initial mixing ratio component A:component B:component M will be 1:1:0, then step-wise changing to 1:1:0.25.

In an alternative embodiment (not shown), the delivery device comprises at least three standard construction cylindrical syringes containing components A, B, and C, with outputs connected via a manifold, with one of the syringes supplying component C which is a diluent, such as water. A valve is provided that allows one to bypass the admixing of component C into the mixture, whereby the diluent can be expressed to drain at the beginning of the coating delivery. At a point during delivery of the coating, the valve is actuated thus directing the diluent into the manifold and admixing the diluent into the composition of components A and B.

In yet a further alternative embodiment (not shown), the delivery device comprises at least two standard construction cylindrical syringes containing components A and B, with outputs connected via a manifold. A valve is provided that allows one to bypass a portion of component B, whereby a portion of component B can be expressed to drain at the beginning or at the end of the coating delivery as needed. At a point during delivery of the coating, the valve is actuated thus directing a pre-selected portion of component B into the manifold and admixing component B at a different ratio with component A, resulting in a coating with different properties.

It should be clear that the present invention may be practiced in a variety of ways. These include, for instance, providing the functions or physiological properties of the compositions delivered from a single delivery device shown in Table 2 below:

TABLE 2

| Case | Function 1 | Function 2 | Function 3 | Function 4 |
|---|---|---|---|---|
| 1 | Adhesive | Sealant | | |
| 2 | Adhesive | Adhesion Preventative | | |
| 3 | Sealant | Adhesion Preventative | | |
| 4 | Sealant | Hemostat | | |
| 5 | Adhesive | Sealant | Adhesion Preventative | |
| 6 | Adhesive | Hemostat | Sealant | |
| 7 | Adhesive | Hemostat | Sealant | Adhesion Preventative |
| 8 | Hemostat | Sealant | Antimicrobial | |

For example, Case 8 above, summaries an embodiment which has a first composition (i.e. a first mixing ratio) delivered to act as a hemostat, changing step-wise (or continuously) to a second composition (i.e. a second mixing ratio) delivered to act as a sealant, finally changing step-wise (or continuously) to a third composition (i.e. a third mixing ratio) delivering an antimicrobial on top of the sealant.

Figure 19A:
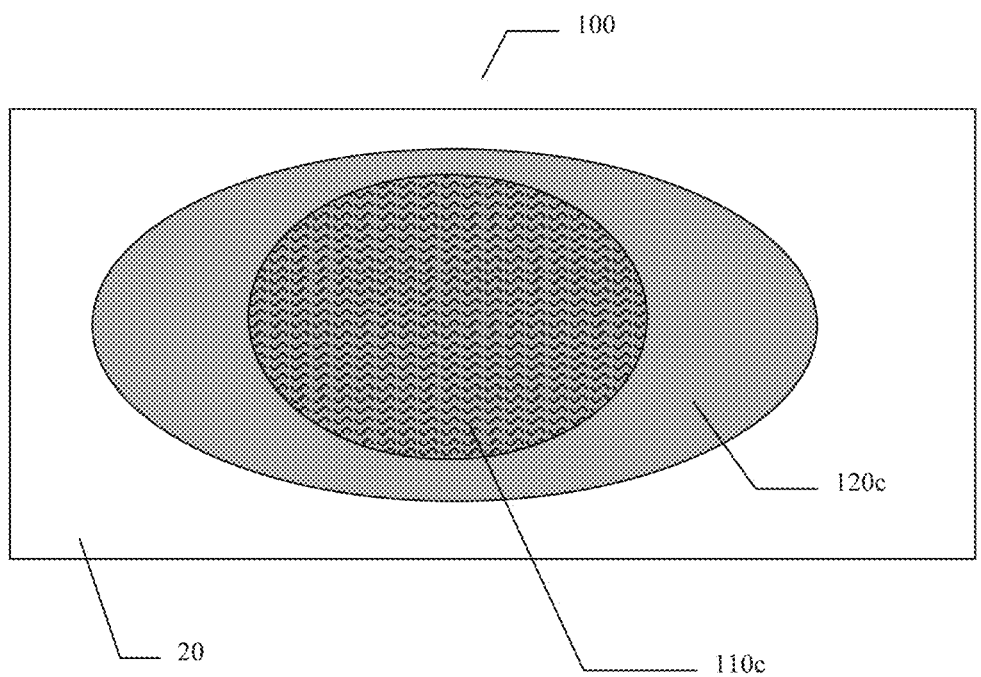
FIGS. 19 A-B shows coating comprising multiple layers and overlap pattern according to an embodiment of the present invention.
Figure 19B:
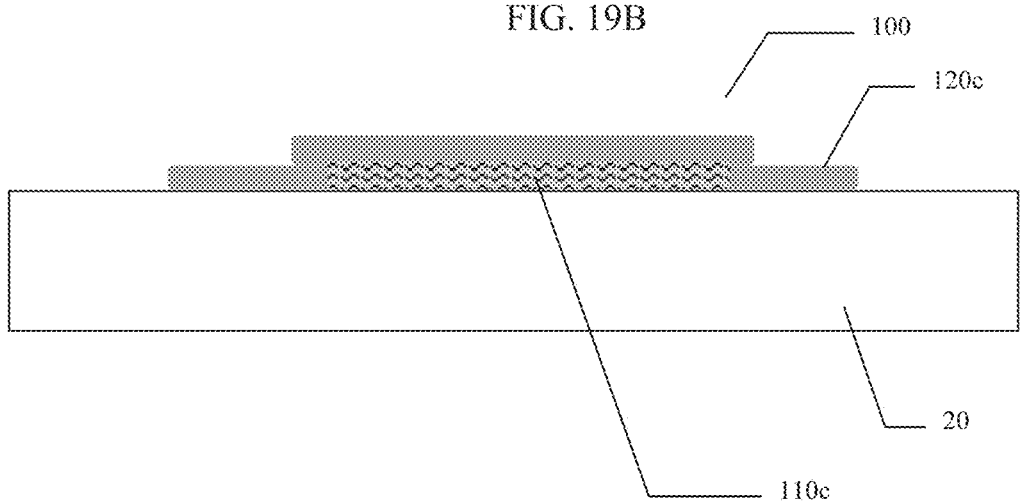

It is to be understood that the present invention may include the use of colorants in one or more of the components for visualization purposes. Motivation for the inclusion of color includes increasing the user's ability to distinguish where a coating has already been applied, as well as the relative thickness of a given layer. We additionally envision providing colorant systems that have the ability to be easily discernible by the naked eye. Further motivation includes the ability to distinguish areas of overlay of individual layers. For instance, a first layer could be applied which would be blue in color to help distinguish where this coating is applied to the bodily tissue. The greater the thickness of the coating layer, the deeper in color the layer would be. A second coating, possibly red in color, could be applied atop the first coating, in which the combined coating would appear purple to the surgeon. Applying this second coating to native, uncoated, tissue would result in a coating red in color. Other color combinations would be apparent to one having ordinary skill; for instance using blue and yellow combinations would result in blue, green, and yellow colors for tissue coated by the first, the first and second, and the second coatings, respectively. This would be a clinically relevant advantage to the surgeon and provide benefit to the patent. Referring now to FIG. 19A, showing a schematic top view, and 19B, showing a schematic cross-sectional view, coating 100 is shown formed on tissue 20 with coating 100 shown comprising layer 110c on tissue 20 and layer 120c formed on top of layer 110c and extending beyond layer 110c to coat larger area of tissue 20. To be clear, as can be seen in this particular embodiment, layer 110c is delivered first and is then covered on top by layer 120c having a wider area and covering layer 110c fully and extending beyond layer 120c. Layer 110c is shown in FIG. 19A as visible through layer 120c which is on top of layer 110c. In a further embodiment, the depth of a hue of color will be changing with the ratio of components changing, i.e. when colored component is delivered at a ratio of 1:1 to non-colored component the coloration being light, after switching to 4:1 ratio colored component to non-colored component, the coloration will change to deep color, with even deeper color in the areas of overlap of 1:1 and 4:1 compositions. While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims.

We claim:

1. A method for applying on tissue a coating having at least two physiologically distinct layers from a single device by delivery of a multi-part biomedical composition in different blended or mixing ratios comprising the steps of
   a) connecting at least two syringe barrels that contain inter-reacting components of the multi-part biomedical composition, said barrels each having a piston that is internally slidable for expression of said components, wherein at least a first syringe comprises a first retention compartment and a second retention compartment that are spaced axially therein with a gasket positioned in the first retention compartment;
   b) advancing the pistons through each syringe barrel to express onto a surface the inter-reacting components of the multi-part biomedical composition in a first blended or mixing ratio;
   c) continuing to advance the pistons to engage the gasket with the piston of the first syringe or to disengage the gasket from the piston of the first syringe at a point between the first retention compartment and the second retention compartment;
   d) still further advancing the pistons through each syringe barrel to express the inter-reacting components of the multi-part biomedical composition in a second blended or mixing ratio to form a coating having physiologically observably distinct layers.

2. The method of claim 1, wherein the multi-part biomedical composition at the first blended or mixing ratio in its final form has physiologically observable properties selected from the group consisting of anti-adhesion, sealant, adhesive and hemostatic; and wherein the multi-part biomedical composition at the second blended or mixing ratio has physiologically observable properties in its final form selected from the group consisting of anti-adhesion, sealant, adhesive and hemostatic.

3. The method of claim 2, wherein the multi-part biomedical composition at the first blended or mixing ratio in its final form has physiologically observable properties that are different from the physiologically observable properties of the multi-part biomedical composition at the second blended or mixing ratio in its final form.

4. The method of claim 3, wherein the multi-part biomedical composition at the first blended or mixing ratio in its final form has physiologically observable properties selected from the group consisting of: sealant, adhesive and hemostatic; and wherein the multi-part biomedical composition in the second blended or mixing ratio in its final form has anti-adhesion properties.

5. The method of claim 1, wherein the physiologically observably distinct layers overlap at least in part and optionally have different colors.

* * * * *